US009622487B2

(12) United States Patent
Meyer et al.

(10) Patent No.: US 9,622,487 B2
(45) Date of Patent: Apr. 18, 2017

(54) ANNUAL BROME CONTROL USING A NATIVE FUNGAL SEED PATHOGEN

(75) Inventors: Susan Elizabeth Meyer, Elk Ridge, UT (US); Suzette Clement, Mapleton, UT (US); Julie Beckstead, Spokane, WA (US)

(73) Assignees: The United States of America as Represented by the Secretary of Agriculture, Washington, DC (US); Gonzaga University, Spokane, WA (US)

( * ) Notice: Subject to any disclaimer, the term of this patent is extended or adjusted under 35 U.S.C. 154(b) by 575 days.

(21) Appl. No.: 13/560,828

(22) Filed: Jul. 27, 2012

(65) Prior Publication Data

US 2013/0035231 A1    Feb. 7, 2013

Related U.S. Application Data

(60) Provisional application No. 61/514,811, filed on Aug. 3, 2011.

(51) Int. Cl.
*A01N 63/04* (2006.01)
*A01B 79/00* (2006.01)
*A01P 13/00* (2006.01)

(52) U.S. Cl.
CPC .................. *A01N 63/04* (2013.01)

(58) Field of Classification Search
CPC ..... A01N 63/04; A01N 25/08; A01N 2300/00
See application file for complete search history.

(56) References Cited

U.S. PATENT DOCUMENTS 3,083,089 A  *   3/1963   Renner .................... 504/126
5,332,673 A      7/1994   Harris
6,008,159 A  *  12/1999   Medd et al. .............. 504/177

OTHER PUBLICATIONS

Stewart, T. E. The Grass Seed Pathogen Pyrenophora Semeniperda as a Biocontrol Agent for Annual Brome Grasses, Brigham Young University: Thesis, Aug. 2009.*
Beckstead J, et al., "Cheatgrass facilitates spillover of a seed bank pathogen onto native grass species," 2010 J Ecology 98: pp. 168-177.
Beckstead J, et al., "A race for survival: Can Bromus tectorum seeds escape Pyrenophora semeniperda-caused mortality by germinating quickly?," 2007 Annals of Botany 99: pp. 907-914.
Meyer SE, et al., "The quick and the deadly: growth vs virulence in a seed bank pathogen," 2010 New Phytol 187: pp. 209-216.
Campbell MA, et al., "Optimizing conditions for growth and sporulation of Pyrenophora semeniperda," 2003 Plant Path 52: pp. 448-454.
Ooi M, et al., "Comparison of the cut and tetrazolium tests for assessing seed viability: a study using Australian native *Leucopogon* species," 2004 Ecol Manage & Restor 5: pp. 141-143.
Campbell MA, et al., "Growth and sporulation of Pyrenophora semeniperda in vitro: effects of culture media, temperature and pH," 1996 Mycol Res 100: pp. 311-317.
Dooley Sr, Beckstead J, "Characterizing the interaction between a fungal seed pathogen and a deleterious rhizobacterium for biological control of cheatgrass," 2010 Biol Control 53: pp. 197-203.
Meyer SE, et al., "Annual Brome Biocontrol after Wildfire Using a Native Fungal Seed Pathogen," JFSP Project No. 2007-1-3-10.
Meyer SE, et al., "Impact of the pathogen Pyrenophora semeniperda on Bromus tectorum seedbank dynamics in North American cold deserts," 2006 Weed Research 47: pp. 54-62.
Meyer SE, et al., "Cheatgrass (Bromus tectorum) Biocontrol Using Indigenous Fungal Pathogens," 2008 USDA FS RMRS-P-52: pp. 61-67.
Meyer SE, et al., "A seedbank pathogen causes seedborne disease: Pyrenophora semeniperda on undispersed grass seeds in western North America," 2008 Can J Plant Pathol 30: pp. 525-533.
Stewart TE, Allen PS, "First Report of Pyrenophora semeniperda in Turkey and Greece," 2009 Plant Disease 93: p. 1351.
Stewart TE, "The Grass Seed Pathogen Pyrenophora semeniperda as a Biocontrol Agent for Annual Brome Grasses," Aug. 2009 Thesis BYU.

* cited by examiner

*Primary Examiner* — Ali Soroush
*Assistant Examiner* — Genevieve S Alley
(74) *Attorney, Agent, or Firm* — John Fado; John Dellinger; Janet I. Stockhausen

(57) ABSTRACT

Formulations having a selective, mycoherbicide activity for killing ungerminated seeds of invasive grass species are provided. An agricultural, mycoherbicide formulation is taught for killing ungerminated seeds of invasive grass species. The formulations can comprise, for example, a slow-growing strain of *Pyrenophora semeniperda*, a fast-growing strain of *Pyrenophora semeniperda*, or a combination thereof, and an agriculturally acceptable carrier. As such, the teachings include a composition comprising a mixture of a slow-growing strain of *Pyrenophora semeniperda* and a fast-growing strain of *Pyrenophora semeniperda*. The mixture of strains can be used to provide a mixture of virulence that is useful for killing carryover seed banks, with regard to both type and level of virulence.

12 Claims, 8 Drawing Sheets

FIG. 1.

ANNUAL BROME CONTROL USING A NATIVE FUNGAL SEED PATHOGEN

CROSS-REFERENCE TO RELATED APPLICATIONS

This application claims the benefit of U.S. Provisional Application Nos. 61/514,811, filed Aug. 3, 2011, which is hereby incorporated herein by reference in its entirety,

STATEMENT REGARDING FEDERALLY SPONSORED RESEARCH OR DEVELOPMENT

This invention is jointly owned with and was made with United States Government support under Joint Venture Agreement 07-JV-11221673-345 awarded by the USDA Forest Service. The Government has certain rights in this invention.

BACKGROUND OF THE INVENTION

Field of the Invention

This application is generally directed to a selective, mycoherbicide formulation for killing ungerminated seeds of invasive grass species.

Description of the Related Art

Annual grass weeds cause large yield losses in intensive agriculture, and more importantly from a Forest Service perspective, are principal contributors to environmental degradation on vast acreages of public land in the western United States. Federal, state, and local public landowners, as well as private landowners, and in particular winter cereal grain producers, suffer this condition in one of our most important resources—our land. This condition is present in millions of hectares of land that are important to rangeland, and also in cropland, for example. Moreover, not only do these weeds take over the land, they also add substantially to the fire hazard in semi-arid and arid regions. As such, the art would appreciate a method of treating soil to prevent, inhibit, or eliminate stands of invasive grass species in such areas, and particularly, a method of restoring semi-arid and arid rangeland.

A major obstacle to seeding success with native species as part of post-burn rehabilitation in arid and semi-arid shrubland ecosystems is competition from exotic annual brome grasses such as cheatgrass (*Bromus tectorum*) and red brome (*Bromus rubens*). In many cases, these are the same grass species that fueled the shrub-destroying fire. Seed banks of annual bromes are depleted but usually not completely destroyed by burning. The common wisdom is to seed as quickly as possible after the fire that destroys the shrub overstory, in order to give the seeding a chance to establish before annual brome competition builds back up. In arid and semi-arid ecosystems, seedings often fail because of inadequate precipitation, and this window of opportunity closes quickly. Once annual bromes reestablish dominance after the shrub-destroying fire, it becomes very difficult to seed successfully on these sites, even if they reburn. This is because more brome seeds survive fire when hot-burning woody fuels are no longer present. If we could find a way to destroy the residual annual brome seed bank after fire, the probability of successful rehabilitation would be greatly increased, and even sites that (i) have burned many times and (ii) are in persistent annual brome monocultures could perhaps be seeded successfully.

The options available for control of annual brome grasses in arid and semi-arid wildland ecosystems are limited, and each has disadvantages. The options include, for example, burning, tillage, and the application of pre- and post-emergence chemicals (herbicides). Early season burning, before seed dispersal, can eliminate most current-year seeds, but there may still be carryover seeds in the seed bank, and these seeds can provide significant competition for seeded species in the years following treatment. Also, prescribed burning in these ecosystems is risky and raises other issues, such as air quality. Tillage after annual brome emergence is too expensive to undertake on large acreages, damages remnant perennials, and causes soil disturbance. Herbicides tend to be expensive, and selectivity of the herbicides also poses concern, as well as the length of time that they can negatively impact the environment after application. The detailed, habitat-specific research needed to understand herbicide impact on non-target species is often not in place to guide management. And, there are many policy issues surrounding the use of herbicides.

One of skill will appreciate that the current practices of controlling brome grass have several problems. A major problem to note, however, is that currently available methods do little or nothing to eliminate ungerminated seeds, and since annual grass weeds respond dramatically to increases in available resources, even a few ungerminated carryover seeds can quickly re-establish a population. As such, an effective control for these grass weeds should include elimination of this bank of ungerminated seeds.

Accordingly, one of skill will appreciate a biocontrol method for elimination of annual grass weed persistent seed banks in rangeland and cropland, the method (i) reducing or eliminating the repeated or extensive use of fire, tillage and chemicals and the environmental effects of such use; (ii) reducing costs; (iii) increasing target selectivity; (iv) facilitating use on large acreage; (iv) functioning to reduce or eliminate seed carryover from a persistent seed bank; and, namely, (v) eliminating or otherwise controlling banks of ungerminated seeds. There is currently no other biocontrol method for killing ungerminated seeds.

SUMMARY OF THE INVENTION

This application is generally directed to a selective, mycoherbicide formulation for killing ungerminated seeds of invasive grass species.

In some embodiments, the teachings are directed to an agricultural, mycoherbicide formulation for killing ungerminated seeds of invasive grass species, the formulation comprising a slow-growing strain of *Pyrenophora semeniperda*, a fast-growing strain of *Pyrenophora semeniperda*, and an agriculturally acceptable carrier. In these embodiments, the formulation functions to kill ungerminated seeds of an invasive grass species. As such, in some embodiments, the teachings provided herein are directed to a composition comprising a mixture of a slow-growing strain of *Pyrenophora semeniperda* and a fast-growing strain of *Pyrenophora semeniperda*.

The relative growth rates of strains can be determined using any method known to one of skill. In some embodiments, the slow-growing strain is limited to reaching a mycelial colony diameter of <50 mm after 14 days at 20° C. on quarter-strength potato dextrose agar from a single conidial inoculation. And, in some embodiments, the fast-growing strain is limited to reaching a mycelial colony diameter of >65 mm after 14 days at 20° C. on quarter-strength potato dextrose agar from a single conidial inoculation.

The carrier can be used to form particles for the formulations. The formulation can comprise, for example, the slow-growing strain on the agriculturally acceptable carrier in the form of particles comprising a non-swelling calcined montmorillonite clay material, the particles having a diameter ranging from about 0.200 mm to about 1.000 mm.

It should be appreciated that the invasive grass species can be any invasive grass species prevented, inhibited, or eliminated using the teachings provided herein. In some embodiments, the invasive grass species comprises a Japanese brome (*Bromus arvensis*), a ripgut brome (*Bromus diandrus* or *Bromus rigidus*), or a medusa head (*Taeniatherum caput-medusae*). In some embodiments, the compositions and formulations taught herein are designed to kill cheatgrass (*Bromus tectorum*) and, in some embodiments, the compositions and formulations taught herein are designed to kill red brome (*Bromus rubens*).

The methods provided herein are the only methods known in the art for killing ungerminated seeds of invasive grass species. As such, the teachings provided herein include methods of treating soil to prevent, inhibit, or eliminate stands of invasive grass species. In some embodiments, the methods comprise administering an effective amount of a *P. semeniperda* formulation to a soil in need of a prevention, inhibition, or elimination of a stand of an invasive grass species; wherein, the administering is done after a dispersal of seeds of the invasive grass species into the soil and prior to a germination-inducing rain. These embodiments include a co-administering of an effective amount of an emerged seedling control agent. In some embodiments, the emerged seedling control agent can be selected from the group consisting of (i) a burn that is administered either before or after the administration of the *P. semeniperda*; (ii) a tillage that is administered after the germination-inducing rain, and thus always after the administration of the *P. semeniperda*; (iii) a pre-emergent herbicide that is administered before, during, or after administration of the *P. semeniperda*, as long as it's before the germination-inducing rain; (iv) a post-emergent herbicide that is administered after the germination-inducing rain, and thus always after the administration of the *P. semeniperda*; (v) a second mycoherbicide that is administered before, during, or after administration of the *P. semeniperda*; (vi) and a bacterial biocontrol that is administered before, during, or after administration of the *P. semeniperda*.

In some embodiments, the method includes eliminating at least 95% of the seeds of a target invasive species from the soil. And, in some embodiments, the method includes eliminating at least 98% of the seeds of a target invasive species from the soil.

In some embodiments, the soil is an arid, or semi-arid, rangeland. In some embodiments, the soil is a cropland soil. And, in some embodiments, the soil supports a desired intact vegetation. The desired intact vegetation can be, for example, a desert, or semi-desert, shrub community.

A variety of methods of sporulating and applying the mycoherbcides were also tested, and valuable formulations and methods of application were identified, In some embodiments, an agricultural, mycoherbicide formulation for killing ungerminated seeds of invasive grass species can comprise a strain of *Pyrenophora semeniperda* produced using a process comprising sporulation of the strain in a MAM supplement (a modified alpha cell broth of coconut milk and oatmeal); and, an agriculturally acceptable carrier in the form of particles comprising a vermiculite material, the particles having a diameter ranging from about 0.200 mm to about 1.000 mm. And, in some embodiments, an effective amount of such a formulation can be administered to a soil in need of a prevention, inhibition, or elimination of a stand of an invasive grass species. The administration can include a co-administering of an effective amount of an emerged seedling control agent selected from the group consisting of a burn, a tillage, a pre-emergent herbicide, and a post-emergent herbicide, a second mycoherbicide, and a bacterial biocontrol; wherein, the administering is done after a dispersal of seeds of the invasive grass species into the soil and prior to a germination-inducing rain.

BRIEF DESCRIPTION OF THE DRAWINGS

FIGS. 1A and 1B illustrate frequency distribution of isolates or strains in different Type 2 virulence categories was quite similar between trials, according to some embodiments.

DETAILED DESCRIPTION OF THE INVENTION

Figure 2:
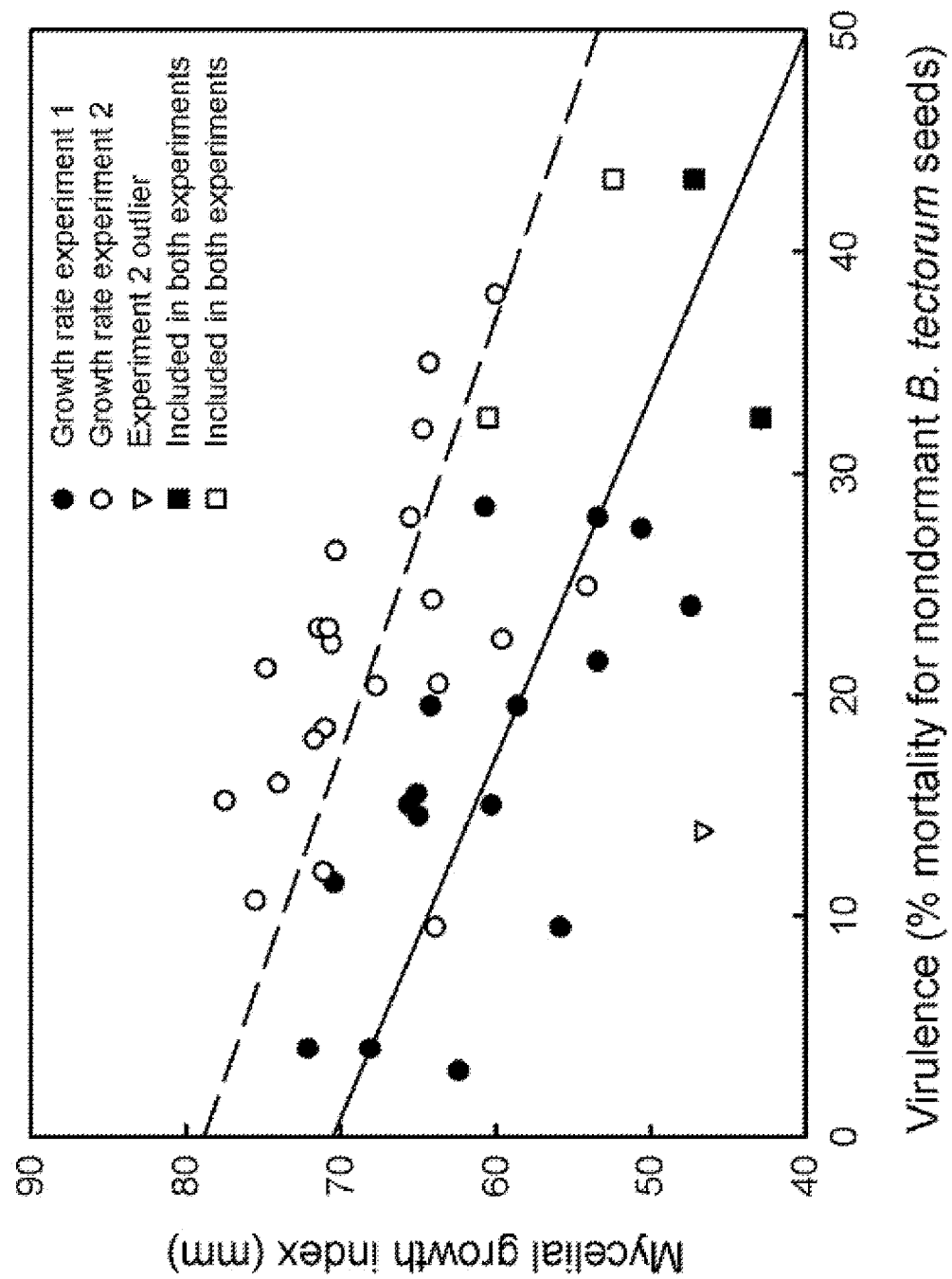
FIG. 2 illustrates the negative relationship between Type 2 virulence and mycelial growth index, according to some embodiments.

This application is generally directed to a selective, mycoherbicide formulation for killing ungerminated seeds of invasive grass species. In some embodiments, the teachings are directed to an agricultural, mycoherbicide formulation for killing ungerminated seeds of invasive grass species, the formulation comprising a slow-growing strain of *Pyrenophora semeniperda*, a fast-growing strain of *Pyrenophora semeniperda*, and an agriculturally acceptable carrier. As such, in some embodiments, the teachings provided herein are directed to a composition comprising a mixture of a slow-growing strain of *Pyrenophora semeniperda* and a fast-growing strain of *Pyrenophora semeniperda*. In some embodiments, the mixture of strains can be formed into any ratio of fast strain to slow strain that provides a desired result with regard to the teachings provided herein. In some embodiments, the fast strain:slow strain ratio can range from 6:1 to 1:6, from 5:1 to 1:5, from 4:1 to 1:4, from 3:1 to 1:3, from 2:1 to 1:2, to 1:1.

The mixture of strains provides a mixture of virulence, with regard to both type and level of virulence. The term "low Type 1 virulence" can be used to refer to less than 10% dormant seed mortality when applied at 1:6400 inoculum dilution after incubation at 20 C for 2 weeks. The term "high Type 1 virulence" can be used to refer to greater than 30% dormant seed mortality at 1:6400 inoculum dilution after incubation at 20 C for 2 weeks. The term "intermediate Type 1 virulence" can be used to refer to a range from about 10% to about 30% dormant seed mortality when applied at 1:6400 inoculum dilution after incubation at 20 C for 2 weeks. The term "low Type 2 virulence strains" can be used to refer to strains that can only kill <10% of non-dormant cheatgrass seeds after inoculation at saturating loads and incubation for 4 weeks at about 20° C. The term "high Type 2 virulence strains" can be used to refer to strains that can kill >30% of non-dormant cheatgrass seeds after inoculation at saturating loads and incubation for 4 weeks at about 20° C. And, the term "intermediate Type 2 virulence strains" can be used to refer to strains that can kill 10-30% of non-dormant cheatgrass seeds after inoculation at saturating loads and incubation for 4 weeks at about 20° C. One of skill will appreciate that the time and temperature can be varied, for example, from about 15° C. to about 25° C.; from about 15° C. to about 20° C., from about 20° C. to about 25° C., or any range therein; and, from about 7 days to about 14 days, from about 10 days to about 30 days, from about 14 days to about 28 days, or any range therein, in some embodiments, where the relative measure should be taken at the same, or substantially the same, time and temperature between samples.

Type 1 virulence measured using this method is weakly positively correlated with ability to kill seeds at low loads using bulk inoculum in laboratory infection trials in seed zone microcosms (steel rings containing autoclaved natural seed zone cores from the field using the ring bioassay procedure of Beckstead et al., Journal of Ecology (1) 98:168-177 (2010). Type 1 virulence and Type 2 virulence are not positively correlated among strains. However, Type 1 virulence is weakly positively correlated with mycelial growth rate.

Ungerminated seeds can be dormant seeds, and the determination of whether a seed is ungerminated or dormant can be made using any method known to one of skill. The term "dormant seeds" can be used to refer to seeds that require at least 6-8 days to germinate under optimum temperature conditions of about 20° C., and the term "non-dormant seeds" can be used to refer to seeds that can germinate in 1-6 days under optimum temperature conditions of about 20° C.

The terms "composition," "compound," "inoculant," and "pathogen" can be used interchangeably in some embodiments and, it should be appreciated that a "formulation" can comprise an inoculant or pathogen presented herein. In some embodiments, the formulation is administered in combination with burning, tillage, or an herbicide, and the combination administration can be referred to as a "system." Likewise, in some embodiments, the active components can also be referred to as an "agent," a "bioactive agent," or an "herbicide" whether alone, or in an agriculturally acceptable composition or formulation. An inoculant or formulation as taught herein should be stable.

An inoculant or formulation can be considered as "stable" if it loses less than 10% of its original activity. For example, the stability of a formulation can be measured by comparing its activity immediately after making the formulation to its activity at the time of administration, and this can include a reasonable shelf life, in some embodiments. In some embodiments, the formulation can be considered as stable if the formulation loses less than 5%, 3%, 2%, or 1% of its original activity when comparing its activity immediately after making the formulation to its activity at the time of administration, and this can include a reasonable shelf life, in some embodiments.

An inoculant or formulation can be considered as "substantially stable" if its formulation loses less than about 10% of its original activity, as long as it can perform its intended use to a reasonable degree of efficacy, as determined as useful by one of skill. In some embodiments, a "reasonable degree of efficacy" can be 75%, 80%, 85%, 90%, 95%, 97%, 99%, or any percentage therein, in 1% increments, where the term "efficacy" can be used to refer to the percentage of seeds killed using the ring bioassay procedure of Beckstead et al., Journal of Ecology (1) 98:168-177 (2010). The loss can be measured, as above, by comparing its activity after making the formulation to the time of administration, and this can include a reasonable shelf life, in some embodiments. In some embodiments, a formulation or inoculant can be considered as substantially stable if it loses greater than about 2%, about 5%, about 7%, about 9%, about 10%, of its original activity. The loss may be measured by comparing its activity after making the inoculants or formulation to the time of administration, and this can include a reasonable shelf life, in some embodiments. In some embodiments, an inoculant or formulation is stable or substantially stable, if useful for a period ranging from about 1 month to about 3 months, from about 1 month to a year, from 3 months to a year, from 3 months to 2 years, from 3 months to 3 years.

Making the Inoculant

One of skill will appreciate that, at least from the teachings provided herein, there are a wide variety of possible formulations that can be selected and designed for administration at a given target site, the selection of which is, at least in part, dependent on the site to be treated. The design of the formulation can include for example, (i) identifying the target site; (ii) identifying the present condition of the target site, such as whether it has intact vegetation or is post-burn; (iii) selecting an inoculant, for example, slow strain, fast strain, or mix of slow and fast strains; (iv) selecting a carrier; and (v) selecting a co-treatment for elimination of seedlings, such as burning, tillage, or herbicide, for co-administration at the target site.

The term "target site" can be used to refer to a select location to be treated, in which the target site comprises a seed bank having annual grass weed seeds, referred to herein as "a target invasive species", that could be killed, infected, or otherwise reduced in carryover using the methods provided herein. One of skill will appreciate that the target site can include any location arid, semi-arid, or otherwise, that would benefit from any of the compositions or formulations provided herein. The terms "treat," "treated," "treating," and "treatment" can be used interchangeably and refer to the administering or application of the formulations taught herein directed to the prevention, inhibition, or elimination of stands of invasive grass species.

In some embodiments, the formulation comprises a slow-growing strain of *Pyrenophora semeniperda*, a fast-growing strain of *Pyrenophora semeniperda*, and an agriculturally acceptable carrier. In these embodiments, the formulation functions to kill ungerminated seeds of an invasive grass species. As such, in some embodiments, the formulation comprises a composition having a mixture of a slow-growing strain of *Pyrenophora semeniperda* and a fast-growing strain of *Pyrenophora semeniperda*.

The relative growth rates of strains can be determined using any method known to one of skill. In some embodiments, for example, the slow-growing strain is limited to reaching a mycelial colony diameter of <50 mm after 14 days at 20° C. on quarter-strength potato dextrose agar from a single conidial inoculation. And, in some embodiments, for example, the fast-growing strain is limited to reaching a mycelial colony diameter of >65 mm after 14 days at 20° C. on quarter-strength potato dextrose agar from a single conidial inoculation.

The term "fast-growing strains" can be used to refer to strains that reach a mycelial colony diameter >65 mm after 14 days at about 20° C. on quarter-strength potato dextrose agar from a single conidial inoculation. The term "slow-growing strains" can be used to refer to strains that reach a mycelial colony diameter of <50 mm after 14 days at about 20° C. on quarter-strength potato dextrose agar from a single conidial inoculation. The term "intermediate-growing strains" can be used to refer to strains that reach a mycelial colony diameter of 50 to 65 mm after 14 days at about 20° C. on quarter-strength potato dextrose agar from a single conidial inoculation.

The compositions of the invention may be formulated as granules, wettable powders, emulsifiable concentrates, powders or dusts, flowables, solutions, suspensions or emulsions, or as controlled release forms such as microcapsules. In some embodiments, these formulations can contain from about 0.5% to about 95%, from about 1.0% to about 98%, from about 2.0% to about 90%, from about 5.0% to about 85%, from about 10.0% to about 80%, from about 15% to about 75%, from about 20% to about 65%, from about 25% to about 50%, from about 30% to about 40%, or any range therein, by weight of active ingredients. The optimum amount for any given compound will depend on formulation, application equipment and nature of the invasive species to be controlled.

The term "about" can be used to refer to a possible variation in an amount or condition that would not be expected by one of skill in the art to create a significant difference in performance of a recited claim or claim limit such as, for example, in a function, a measure, or an effect. Likewise, the terms "substantial" or "substantially" can be used to (i) refer to a difference in an amount or condition that would be expected by one of skill in the art to create a significant difference in performance of a recited claim or claim limit such as, for example, in a function, a measure, or an effect; or (ii) an approximate equivalence in an amount or condition that would not be expected by one of skill in the art to create a significant difference in performance of a recited claim or claim limit such as, for example, in a function, a measure, or an effect.

An "agriculturally acceptable carrier" is a diluent, adjuvant, excipient, or vehicle with which the inoculant is administered. A carrier is agriculturally acceptable when it has been determined to be environmentally safe including, but not limited to, safe to plants, animals, and fungi. Such carriers can be readily identified by those of skill. An example of an agriculturally acceptable carrier is AGSORB (available from Monsanto Agricultural Co.), available, for example, in compositions that comprise montmorillonite, attapulgite, and hydrous aluminosilicate. In some embodiments, an agriculturally acceptable carrier can include agricultural waste products such as, for example, corncob grits. In some embodiments, an agriculturally acceptable carrier is a solid having a bulk density that is less than 1.0 g/ml, 0.8 g/ml, 0.6 g/ml, or 0.4 g/ml. In some embodiments, the carrier can be used to form particles for the formulations. The formulation can comprise, for example, the slow-growing strain on the agriculturally acceptable carrier in the form of particles comprising a calcined montmorillonite material, the particles having a diameter ranging from about 0.200 mm to about 1.000 mm.

Examples of solid carriers include fertilizer, sand, Fuller's earth, attapulgite clay, bentonite clays, montmorillonite clay, vermiculite, perlite, calcium carbonate, brick, pumice, pyrophyllite, kaolin, dolomite, plaster, wood flour, wheat flour, ground corn cobs, ground peanut hulls, ground walnut shells, cotton seed hulls, lignin, sodium silicate, magnesia, mica, iron oxide, zinc oxide, talc, titanium oxides, antimony oxide, cryolite, gypsum, diatomaceous earth, calcium sulphate and other known organic or inorganic materials which absorb or which can be coated with the active compound.

The solid carriers can result in granular formulations that can include relatively coarse particles ranging in size, for example, from about 0.200 mm to about 1.00 mm, from about 0.250 mm to about 0.950 mm, from about 0.300 mm to about 0.900 mm, from about 0.350 mm to about 0.850 mm, from about 0.400 mm to about 0,800 mm, from about 0.450 mm to about 0.750 mm, from about 0.500 mm to about 0.700 mm, from about 0.250 mm to about 0.600 mm, or any range therein considered functional for a particular administration by one of skill in the art.

In some embodiments, we can use particles ranging in size in diameter from about 0.200 mm to about 4.00 mm, from about 0.300 mm to about 3.50 mm, from about 0.400 mm to about 3.00 mm, from about 0.500 mm to about 2.50 mm, from about 0.600 mm to about 2.00 mm, from about 0.700 mm to about 1.50 mm, from about 0.800 mm to about 1.00 mm, from about 1.00 mm to about 3.00 mm, from about 1.50 mm to about 2.50 mm, or any range therein. In some embodiments, the carrier can comprise particles having a diameter of about 0.250 mm, about 0.500 mm, about 0.750 mm, about 1.00 mm, about 1.25 mm, about 1.50 mm, about 1.75 mm, about 2.00 mm, about 2.25 mm, about 2.50 mm, about 2.75 mm, about 3.00 mm, or any 0.100 mm increment therein.

A carrier may be a liquid carrier that does not promote germination. For example, a carrier can be an aqueous carrier, but it should include a germination-retarding but nontoxic additive. Also, the carrier can be a non-aqueous carrier, such as a tackifier or oil, including those used in herbicides and other agricultural products. In some embodiments, the water potential of the seed is reduced to retard germination by adding a solute to an aqueous carrier, the solute including, for example, polyethylene glycol having a molecular weight of about 2000 to about 10,000 Daltons, from about 4000 Daltons to about 8000 Daltons, about 6000 Daltons, or any range therein. In some embodiments, the water potential can be reduced using a sugar, or other organic compound that dissolves in water but is not toxic. Examples of liquid carriers include water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane boyer, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like.

Microcapsules include droplets or granules of the active material enclosed in an inert porous shell which allows escape of the enclosed material to the surroundings at controlled rates. Encapsulated droplets can range in size from about 1 to about 50 microns in diameter. The enclosed liquid can constitute about 50 to 95% of the weight of the capsule and may include a carrier in addition to the active compound. Encapsulated granules can be porous with porous membranes sealing the granule pore openings, retaining the active species in liquid form inside the granule pores. Examples of granule materials can include vermiculite, sintered clay, kaolin, attapulgite clay, sawdust and granular carbon. Membrane materials can include natural and synthetic rubbers, cellulosic materials, styrene-butadiene copolymers, polyacrylonitriles, polyacrylates, polyesters, polyamides, polyureas, polyurethanes and starch xanthates.

Emulsifiable concentrates can include homogeneous liquid compositions dispersible in water with the addition of a non-germinating agent, or other liquid, and may consist entirely of the active compound with a liquid or solid emulsifying agent, or may also contain a liquid carrier, such as xylene, heavy aromatic naphthas, isophorone and other non-volatile organic solvents.

In some embodiments, the formulations can include wetting, dispersing or emulsifying agents. Examples of such agents can include alkyl and alkylaryl sulphonates and sulphates, salts of such compounds, polyhydric alcohols, polyethoxylated alcohols, esters and fatty amines. Such agents may comprise from about 0.1% to about 15%, from about 0.5% to about 10%, from about 1.0% to about 5%, or any range therein in increments of tenths-of-a-percent by weight of a formulation.

The strains can be grown on any suitable medium known to one of skill in the art. For example, the strains can be grown on V8 medium, MAM (a modified alpha cell broth of coconut milk and oatmeal), or both, to increase the conidia, on agar in a Petri dish. After the strains have grown and produced conidia, the Petri dish is harvested using sterile water, and the harvest is collected on a sieve, dried overnight, and scraped off of the sieve to produce a dry inoculant. The dry inoculant is weighed and placed in potato dextrose broth in a fermentor or on a shaker to aerate and grow large quantities of the inoculant. The inoculant can be allowed to grow in the liquid media for about 2-3 days, for example, after which it is centrifuged and decanted from the liquid. The mycelium can then be placed in blender or tumbler and added to a carrier, such as AGSORB, with a supplemental medium to serve as food to promote sporulation. The mix is spread thinly on a tray to dry and covered with a transparent lid to provide light. A suitable light source may provide UV and white light for 2-3 days or longer to facilitate sporulation on the surface of the medium. The thin layer is spread to promote the formation of more spores per unit volume without drying the mix too fast, as the process should include the presence of moisture and light for about 2-14 days.

It should be appreciated that there are several variables that can affect this process of producing the inoculants. Growth time in the fermentor, as well as temperature, for example, can be adjusted to maximize yield. In some embodiments, the time in the fermentor can range from about 2 to about 14 days, from about 2 to about 12 days, from about 3 to about 10 days, from about 4 to about 8 days, from about 2 to about 7 days, from about 3 to about 5 days, from about 2 to about 3 days, or any range therein. In some embodiments, a color change can be an indicator of optimum conditions. Other variables include the amount and type of inoculants that are placed into the fermentor, the fermentor temperature, which can range from about 15-25° C. in some embodiments; and, the media. Drying rate, however, can limit the amount of conidia formed. In some embodiments, the process can be optimized to produce a uniform and complete sporulation. After sporulation is complete, the rate of drying can be increased by increasing the temperature to, for example about 30° C. The media, for example, can include PDB (potato dextrose broth), V8 broth, a sugarbeet byproduct, or MAM.

It should be appreciated that one of skill can vary the type, amount and ratios of seed inoculum that are put in the fermentor. For example, the person of skill could put in the mycelia at different life stages (there are 3; conidia or spores, stromata or fruiting structures sticking out of the seed; and, mycelia), or a combination. The person of skill can also vary the strain (we currently have about 700 strains) by initially screening for virulence or growth rate as an indicator. The use of mycelia can be industrially beneficial, for example, in that it may be easier to grow the mycelia for large scale production in some embodiments than the conidia. The optimal combination may also be a combination of strains.

Methods of Use

The teachings herein provide an agricultural, mycoherbicide composition and formulation for killing ungerminated seeds of invasive grass species. It should be appreciated that the invasive grass species can include any invasive grass species that can be prevented, inhibited, or eliminated using the teachings provided herein. It should be further appreciated that the methods provided herein are the only methods known in the art for killing ungerminated seeds of invasive grass species. As such, the teachings provided herein include methods of treating soil to prevent, inhibit, or eliminate stands of these invasive grass species.

In some embodiments, the method includes eliminating at least 95% of the seeds of a target invasive species from the soil. And, in some embodiments, the method includes eliminating at least 98% of the seeds of a target invasive species from the soil. In some embodiments, at least 90%, 91%, 92%, 93%, 94%, 95%, 96%, 97%, 98%, 99%, 99.5%, 99.7%, 99.9%, and even up to 100% of the seeds can be killed using the teachings provided herein.

In some embodiments, the soil is in an annual grass weed monoculture in arid, or semi-arid, rangeland. In some embodiments, the soil is a cropland soil. And, in some embodiments, the soil supports a desired intact vegetation. The desired intact vegetation can be, for example, a desert, or semi-desert, shrub community. The term "arid" can be used to refer to a geographical region experiencing less than about 8" of annual precipitation. The term "desert" can be used to refer to an arid geographical region. The term "semi-arid" can be used to refer to a geographical region experiencing more than about 8" of annual precipitation and less than about 16" of annual precipitation. The term "semi-desert" can be used to refer to a semi-arid geographical region.

In some embodiments, the invasive grass species comprises a Japanese brome (*Bromus arvensis*), a ripgut brome (*Bromus diandrus* or *Bromus rigidus*), or a medusa head (*Taeniatherum caput-medusae*). In some embodiments, the compositions and formulations taught herein are designed to kill cheatgrass (*Bromus tectorum*) and, in some embodiments, the compositions and formulations taught herein are designed to kill red brome (*Bromus rubens*).

In some embodiments, the invasive species can include species of *Bromus, Genea*, or a combination thereof. In some embodiments, the invasive species is a *Bromus* species. Examples of *Bromus* species that may be controlled using the teachings herein include *Bromus alopecuros* (Weedy Brome), *Bromus arvensis* (Field Brome, Schrader's Brome), *Bromus briziformis* (Rattlesnake Brome, Quake Grass), *Bromus diandrus* (Great Brome, Ripgut Brome, Boyer), *Bromus hordeaceus* (Soft Brome, Bull Grass, Soft Cheat, Soft Chess), *Bromus arvensis* (Japanese Brome), *Bromus madritensis* (Compact Brome), *Bromus rigidus* (Stiff Brome, Ripgut Brome), *Bromus secalinus* (Rye Brome, Chess grass, Cheat Grass), *Bromus sterilis* (Barren Brome, Poverty Brome, Sterile Brome Grass), *Bromus tectorum* (Drooping Brome, Downy Brome).

In some embodiments, the methods comprise administering an effective amount of a *P. semeniperda* formulation to a soil in need of a prevention, inhibition, or elimination of a stand of an invasive grass species; wherein, the administering is done after a dispersal of seeds of the invasive grass species into the soil and prior to a germination-inducing rain. These embodiments include a co-administering of an effective amount of an emerged seedling control agent. In some embodiments, the emerged seedling control agent can be selected from the group consisting of (i) a burn that is administered either before or after the administration of the *P. semeniperda*; (ii) a tillage that is administered after the germination-inducing rain, and thus always after the administration of the *P. semeniperda*; (iii) a pre-emergent herbicide that is administered before, during, or after administration of the *P. semeniperda*, as long as it's before the germination-inducing rain; (iv) a post-emergent herbicide that is administered after the germination-inducing rain, and thus always after the administration of the *P. semeniperda*; (v) a second mycoherbicide that is administered before, during, or after administration of the *P. semeniperda*; (vi) and a bacterial biocontrol that is administered before, during, or after administration of the *P. semeniperda*.

Examples of a burn include a natural burn or a controlled burn. In some embodiments, a natural burn can take place, for example, the summer after seed dispersal but before administration of *P. semeniperda*, and will be ineffective in removing sufficient seeds to prevent stand establishment alone, because of the high densities of dispersed seeds that can survive fire, In some embodiments, a controlled early season burn (in late spring, while seeds are still on the plants) applied the spring previous to administration of *P. semeniperda* will be more effective in destroying current year seed production, but some plants will still be able to establish from nondormant seeds in the seed bank. In some embodiments, a controlled early season burn applied the spring following administration of *P. semeniperda* will be most effective in preventing stand establishment, because it will eliminate seed production from all plants established the previous fall.

Tillage is a method commonly used in agriculture to control annual grass weeds post-emergence but prior to seeding of the winter cereal crop, but has been used on rangelands with limited success. Implements commonly used include moldboard ploughs, rototillers, harrows, tine cultivators, and anchor chains. Tillage could be applied as a seedling control treatment after administration of *P. semeniperda* and after seedling emergence following a germination-inducing rainfall. Applying tillage prior to the germination-inducing rain tends to plant the seeds and is ineffective.

Preemergent herbicides have been used extensively in agriculture and to a lesser extent on rangelands. These chemicals kill germinated seeds and prevent seedling establishment, but have no effect on ungerminated seeds. There are large numbers of preemergent herbicides, but imazapic (e.g., Plateau) is generally the herbicide of choice because it impacts only the germinated seeds of annual plants. The preemergent herbicide chosen must not have an adverse effect on *P. semeniperda* activity. Such a preemergent herbicide could be applied before, during, or after the application of *P. semeniperda*, as long as application takes place before the germination-inducing rain.

Examples of a post-emergent herbicide include ROUNDUP (glyphosate), Post-emergent herbicides would be applied after administration of *P. semeniperda* and after seedling establishment is complete following the germination-inducing rainfall. To ensure complete removal of the established stand, waiting until all fall emergence and any winter/spring emergence is complete is the best strategy, as long as application takes place while plants are still actively growing in the spring.

Examples of bacterial biocontrol agents for reducing growth of targeted annual grass weeds in winter wheat include selected strains of *Pseudomonas syringae, Pseudomonas putida, Enterobacter taylorae*, and *Xanthomonas maltophilia*. The strains have been selected to have inhibitory effects only on the target weeds. These agents are applied in liquid suspension directly to soil shortly before the first germination-inducing rain. They could therefore be applied before, during, or after administration of *P. semeniperda*. These agents reduce weed growth and seed yield but do not necessarily kill emerged seedlings, which limits their usefulness The terms "substantial rain" and "germination-inducing rain" can be used interchangeably in some embodiments and, in some embodiments, can refer to approximately 1" of rain when the temperatures are between about 5° C. and about 25° C.

The terms "administration" or "administering" can be used to refer to a method of incorporating a composition or formulation into the soil, litter, or tissues of a seed of an invasive species in the field, or in the laboratory to test the activity of a formulation or system, for the prevention, inhibition, or elimination of stands of invasive grass species. When the inoculant is administered in combination with an emerged seedling control agent, for example a co-administration, the terms "administration," "administering," "co-administering" and "co-administration," for example, can include sequential or concurrent incorporation of the inoculant with the emerged seedling control agent. The term "sequential" can refer to an administration in series, or overlapping, wherein the onset of the administration of a first agent is before, during, or after the onset of the administration of a second agent, wherein each of the first agent and the second agent can be either a *P. semeniperda* inoculant or an emerged seedling control agent.

An "effective amount" of an inoculant or formulation can refer to an amount which effectively prevents, inhibits, or eliminates a stand of an invasive grass species. An "effective amount" can refer to an amount that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition. The term "efficacy" can refer to a maximum response achievable from an inoculant. Effectiveness can refer to an ability of an inoculant to produce a beneficial effect, for example. In some embodiments, efficacy can be measured by method-effectiveness, which can be used to describe the effect achievable if the inoculant was administered as recommended. In some embodiments, efficacy can be measured by use-effectiveness, which can be the effect obtained under typical use circumstances when adherence is not 100%.

Depending on the formulation, a wide variety of doses can be used. The targeted action and virulence of strains of the inoculants, for example, can allow for the administration of surprisingly low effective doses of the formulations, in some embodiments. As a result, the formulations also improve environmental safety by substantially increasing the separation between an effective dose and any adverse environmental effects.

The active ingredient in the formulation has been determined to be primarily pathogen conidia rather than mycelial fragments, which have low infectivity. The application rate can be determined by quantifying conidial numbers per unit volume or weight of bulk inoculum. These numbers vary widely depending on the formulation, so that the most meaningful expression of application rate is in terms of the conidial numbers applied per unit area. To determine conidial numbers per unit volume of a bulk inoculum, replicated haemocytometer counts can be made from a well-mixed supernatant of a 1:4 (v:v) suspension of bulk inoculum in water. The mean haemocytometer count per unit volume can be converted to a w:v basis by multiplying by the bulk density of the carrier, and the application rate in conidia per unit area can be calculated based on the weight of bulk inoculum applied per unit area. An effective amount of a conidial field application in dose per unit area can range from about $1.0 \times 10^{10}$/ha to $2.0 \times 10^{10}$/ha in some embodiments. In some embodiments, effective doses can range from about $0.1 \times 10^{10}$/ha to about $0.3 \times 10^{10}$/ha. In some embodiments, an effective amount of conidial field application can range from about $0.05 \times 10^{10}$/ha to about $4 \times 10^{10}$/ha, from about $0.07 \times 10^{10}$/ha, to about $3.5 \times 10^{10}$/ha, from about $0.10 \times 10^{10}$/ha to about $3.0 \times 10^{10}$/ha, from about $0.20 \times 10^{10}$/ha, to about $3.0 \times 10^{10}$/ha, from about $0.3 \times 10^{10}$/ha to about $2.5 \times 10^{10}$/ha, from about $0.40 \times 10^{10}$/ha, to about $1.5 \times 10^{10}$/ha, from about $0.50 \times 10^{10}$/ha to about $1.0 \times 10^{10}$/ha, from about $0.60 \times 10^{10}$/ha to about $0.80 \times 10^{10}$/ha, or any range therein. In some embodiments, an effective amount of conidial field application can be about $0.05 \times 10^{10}$/ha, about $0.07 \times 10^{10}$/ha, about $0.09 \times 10^{10}$/ha, about $1.1 \times 10^{10}$/ha, about $1.2 \times 10^{10}$/ha, about $1.3 \times 10^{10}$/ha, about $1.4 \times 10^{10}$/ha, about $1.5 \times 10^{10}$/ha, about $1.6 \times 10^{10}$/ha, about $1.7 \times 10^{10}$/ha, about $1.8 \times 10^{10}$/ha, about $1.9 \times 10^{10}$/ha, about $2.1 \times 10^{10}$/ha, or an $0.05 \times 10^{10}$/ha increment in-between each of these amounts.

In some embodiments, the inoculants and the emerged seedling control agent of the invention may be applied either simultaneously or sequentially. If administered sequentially, the components may be administered in any order in a suitable timescale, for example, with no longer than a selected time between the administration of the inoculants and the emerged seedling control agent. In some embodiments, the inoculants and the emerged seedling agent can be administered within a timescale of a few hours, a few days, a few weeks, or a few months, for example. In some embodiments, a simultaneous (or concurrent) administration may be administered separately, or as a tank mix, a pre-formulated mixture of all the components, or a pre-formulated mixture of some of the components and tank mixed with the remaining components. In some embodiments, the inoculant and emerged seedling control agent can be applied to rangeland in combination or series. In some embodiments, the inoculant and emerged seedling control agent can be applied to an intact vegetation in combination or series. In some embodiments, the inoculant and emerged seedling control agent can be applied to cropland in combination or series. An example of an intact vegetation is sagebrush steppe. An example of a crop can include any vegetation to be harvested as food, livestock fodder, fuel or for any other economic purpose such as, for example wheat, barley, rye, oats, corn, rice, soybeans, alfalfa hay.

In one example, a formulation can be administered to a target site using any means of administration taught herein. In another example, a formulation can be administered by combining the inoculant with cell tissue from the seed for purposes that include, but are not limited to, assays for determining utility and efficacy of an inoculant. And, of course, the formulations and systems can be used to test their stability, activity, toxicity, efficacy, and the like.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1. Isolation and Culturing of a Strain of *Pyrenophora semeniperda*

This example describes two methods to obtain pure cultures of a strain of *Pyrenophora semeniperda*. One isolation method includes the removal of individual stromata from killed seeds ("stromatal isolation method"), and another isolation method includes producing new conidia on killed seeds ("single-sporing method").

Seed bank samples were collected from *B. tectorum* L. monocultures in geographic locations that included Utah, Nevada, Colorado, and Idaho, USA; and, Turkey. In addition, a *B. rubens* sample was obtained from northern Arizona. A steel can, 6 cm in diameter and 4 cm deep, was pushed into the soil until flush with the litter surface. The can was then lifted out with a trowel and its contents were emptied into a labeled paper sack. Samples were air-dried if necessary, screened to remove excess loose soil, and hand-processed to remove all seeds with protruding fungal stromata, as well as all apparently viable seeds. See Beckstead et al., Journal of Ecology (1) 98:168-177 (2010), hereby incorporated herein by reference in its entirety. Ungerminated *B. tectorum*, and the one sample of *B. rubens*, seeds with protruding *P. semeniperda* stromata from each pathogen population were stored air-dry at room temperature in Petri dishes until used for isolation and culturing.

Stromatal Isolation Method

This method includes removal of individual stromata from killed seeds, surface sterilization and plating onto V8 agar using, for example, a method taught in Beckstead et al., Annals of Botany 99:907-914 (2007), which is hereby incorporated herein by reference in its entirety.

Single Sporing Method

Seed bank samples were collected from *B. tectorum L. monocultures* in geographic locations that included western Utah, north-central Nevada, and south-central Washington, USA; and, Turkey. In addition, a *B. rubens* sample was obtained from northern Arizona.

Stromata on killed seeds will usually produce new conidia if they are incubated in water following wounding by breaking off the tip. The new conidia are transferred to a small volume of sterile water using a needle, and the conidial suspension is poured over water agar. Excess water is decanted, and the plates are incubated for 8 hrs at room temperature. Single germinated conidia free of apparent contamination are then transferred using a needle under a dissecting microscope directly to MAM plates for conidial production. For an example method, see, Meyer S E et al. New Phytologist 187:209-216 (2010) which is incorporated herein by reference in its entirety. As an alternative to MAM, for example, V8 agar can be used. In addition, conditions for growth and sporulation of *P. semeniperda* can be optimized using, for example, Campbell M A et al., Plant Pathology 52:448-454 (2003), which is hereby incorporated herein by reference in its entirety.

The isolates were incubated under white and ultraviolet light with a 12 hr photoperiod, at temperatures at or near the optimum of 20° C. Cultures were wounded by scraping after 5-7 days of growth. 5-7 days after wounding, the plates were harvested by rinsing with sterile water onto the surface of a 25-micrometer sieve. Twenty-five 5-cm plates were routinely produced for each isolate. The conidia were allowed to air-dry for several hours on the sieve, and were then scraped free and placed in a small snap-cap glass vial for storage at room temperature until initiation of the tests. Vials were left uncapped overnight to ensure that conidia had fully dried before capping. 5-10% of the isolates failed to yield conidia in culture; these isolates were necessarily excluded from further screening.

Example 2. Virulence Testing

The strains of Example 1 were used in this virulence testing study. To verify viability and vigor before inclusion in virulence trials, the conidial collections were tested for germinability by preparing a conidial suspension in sterile water and casting this onto the surface of a potato dextrose agar (PDA)-coated microscope slide. Conidial germination was measured, usually after 6 hrs at room temperature, by counting the number of germinated conidia out of a total of 100 conidia in each of four independent passes under a compound microscope. Most collections germinated to near 100% within 6 hrs; isolates with very slow germination or low germination percentages (<10% of total isolates) were excluded from the trials.

Virulence trials were carried out using non-dormant *B. tectorum* seeds collected at Whiterocks in Skull Valley, Utah, USA. Uninoculated seeds of this lot germinated to >50% in 1.5 days and to 100% in <4 days at 20° C. A total of 43 isolates was included in the first trial, whereas 35 isolates were included in the second trial. We repeated each of the two virulence trials in time, and each isolate was included as two replications in each time repeat. For each experimental unit, 3 mg of conidia were placed in a small vial with 50 seeds. These were vibrated together using a vortexer to ensure even conidial coverage on the seeds. This usually resulted in a small excess of inoculums not adhering directly to the seeds. This inoculum load is at least two orders of magnitude higher than would probably be encountered under field conditions; the reason for the high load was to attempt to detect maximum among-isolate variation in expressed virulence (seed mortality). The inoculated seeds for each replication were then spread on the surface of two germination blotters (Anchor Paper, St. Paul, Minn., USA) saturated with water and placed in a 10-cm plastic disposable Petri dish. The dishes were stacked randomly into plastic bags to retard water loss and incubated at 20° C. with a 12 hr photoperiod. Dishes were watered as needed for the duration of the experiment and scored at 2, 4, 7, 11 and 15 days. At each scoring, germinated seeds and ungerminated seeds with clear disease signs (protruding black stromata) were counted and removed. At 14 days, ungerminated seeds without disease signs were scored for viability using a cut test that is described, for example, in Ooi M. et al., Ecological Management & Restoration 5:141-143 (2004), which is hereby incorporated by reference herein in its entirety by reference. Usually no ungerminated disease-free seeds remained in the dish. Virulence was calculated from these data as the proportion of total viable seeds that failed to germinate and that also developed disease signs within the 14 day incubation period. These seeds were considered to have been killed by the *P. semeniperda* pathogen.

Mycelial Growth Rates

A pilot growth rate study was performed with four isolates using the protocol of Campbell, M A et al., Mycological Research 100:311-317 (1996), which is hereby incorporated herein in its entirety by reference. The study provided a determination of the number of replicates and the measurement intensity desired to obtain sufficient precision in the full-scale studies. Single germinated conidia from each isolate were inoculated into the centers of ten 10-cm Petri dishes containing quarter-strength PDA. This medium stimulates mycelial growth but not sporulation. The undersurface of each plate was marked with straight lines at 45° intervals across its diameter, providing four axes of measurement for colony diameter. Colony margins were clearly visible from the underside of the plate. We confirmed that, at constant temperature, mycelial colony diameter increased lilnearly with time, and determined that the slope of increase in colony diameter was almost perfectly correlated with day-14 colony diameter (df=2, r=0.999, P<0.01). We therefore decided to use day-14 colony diameter as our index of mycelial growth rate (MGI). We also determined that five replications per isolate provided sufficient precision for distinguishing differences in growth rate among isolates. Full-scale trials were performed using the protocol of five plates per isolate and four colony diameter measurements along the premarked axes after 14 days of incubation at room temperature (ca. 22° C.).

Data from each virulence trial were used to select a subset of isolates representing the full range of virulence phenotypes for mycelial growth rate studies. Eighteen isolates from the first virulence trial were included in the first round of growth rate studies. In the second round, we included 20 new isolates. As a check between the two growth rate studies, we also included two isolates that had been included in the first round, for a total of 22 isolates.

Statistical Analyses

For each virulence trial, we carried out mixed-model ANOVA with isolate as the fixed effect and time repeat as the random effect. We also performed mixed-model ANOVA on the combined dataset to test for a difference in virulence between the two isolate groups. Proportional virulence data were arsine square root transformed before analysis to improve variance homogeneity. We also prepared frequency histograms showing the distribution of isolates into nine virulence categories for each trial.

We analyzed the relationship between MGI and mean virulence using analysis of covariance, with MGI as the dependent variable, mean virulence (seed mortality percentage) as the continuous independent variable and growth rate trial as the class variable. MGI was chosen as the dependent variable because it appeared to vary as a function of trial, allowing variance caused by the effect of trial to be included in the model.

Virulence Results

Virulence varied significantly among isolates in both virulence trials, with a range from 3.0% to 43.3% mean seed mortality in the first trial and from 9.5% to 38.1% in the second trial (Trial 1: $df=42$, 85, $F=6.24$, $P<0.0001$; Trial 2: $df=34$, 66, $F=3.40$, $P<0.0001$). Seed mortality did not vary significantly between virulence trials, averaging 19.4% in the first trial and 21.2% in the second trial (trial main effect: $df=1$, 259, $F=1.45$, $P=0.2294$). We observed no significant difference between time repeats and no significant interaction between isolate and time repeat in the first trial, but, in the second virulence trial, both of these effects were highly significant, with the mean virulence increasing from 18.2% to 24.6% between time repeats (time repeat main effect: $df=1$, 66, $F=18.85$, $P<0.0001$). Eleven isolates showed increases of at least 10% in the second time repeat, but four isolates showed decreases of at least this magnitude (time repeat by isolate interaction; $df=31$, 66, $F=4.21$, $P<0.0001$). The reason for these differences is not known, but they indicate that virulence expression was very sensitive to some uncontrolled environmental variable in the second trial, and that this sensitivity varied by isolate.

Figure 1:
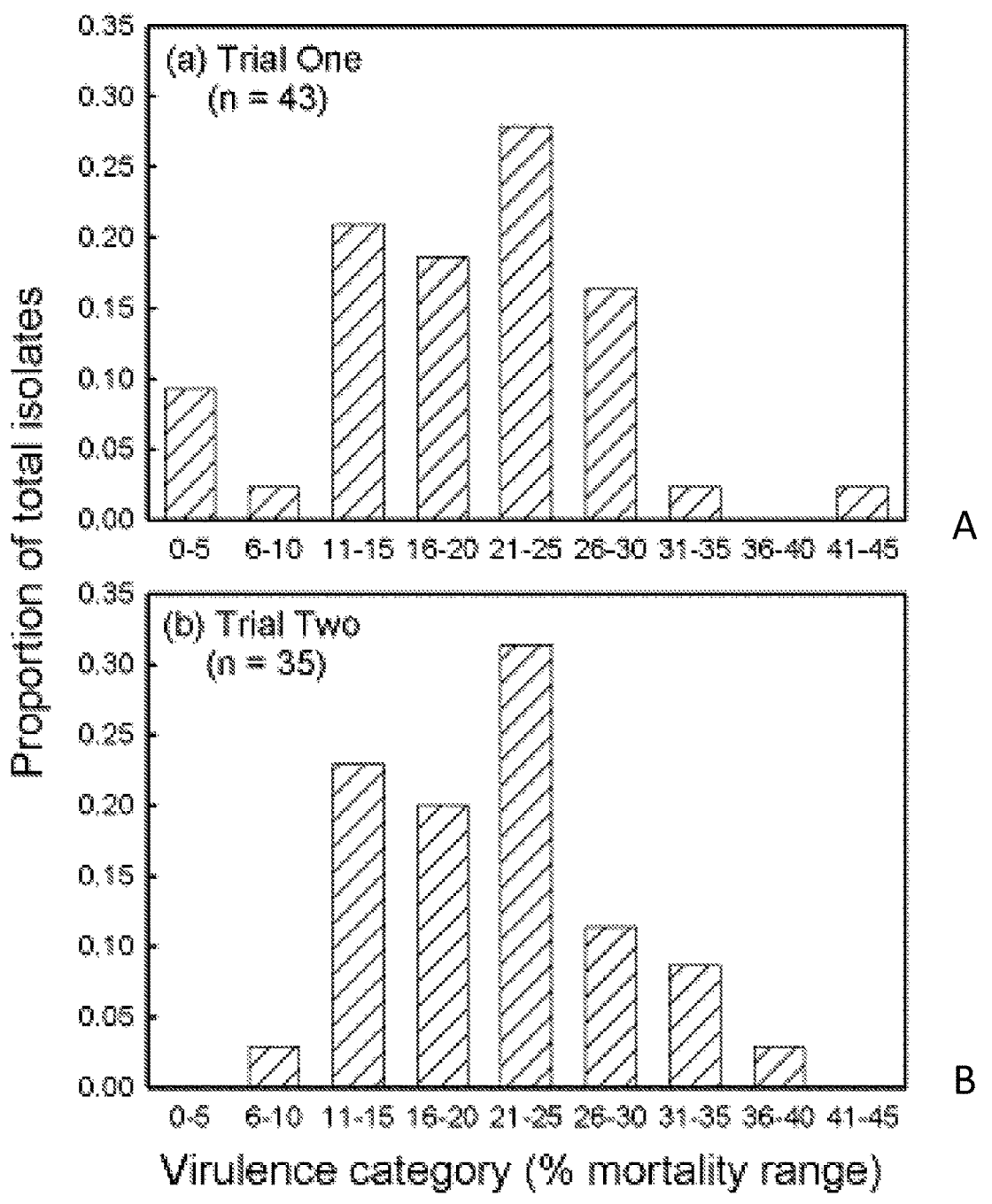

FIGS. 1A and 1B illustrate frequency distribution of isolates or strains in different Type 2 virulence categories was quite similar between trials, according to some embodiments. In the first trial (n=43), the frequency distribution was slightly right skewed, indicating a slight preponderance of less virulent isolates. In the second trial (n=35), the distribution was closer to a normal distribution. In both trials, the great majority of isolates showed low to intermediate virulence, with only six of a total of 78 isolates, or 7.7%, exhibiting virulence >30%.

Mycelial Growth Rate Results

MGI was significantly negatively correlated with virulence percentage in both growth rate trials. This indicated that isolates exhibiting lower virulence were faster growing, whereas those that exhibited higher virulence grew more slowly.

FIG. 2 illustrates the negative relationship between Type 2 virulence and mycelial growth index, according to some embodiments. The ANCOVA (analysis of covariance) virulence percentage main effect: $df=1$, 37, $F=39.84$, $P<0.0001$. The slope of the relationship between virulence percentage and MGI (−0.4354 mm per virulence percentage point) was not significantly different betweens trials (ANCOVA virulence percentage×growth rate trial interaction: $df=1$, 37, $F=0.33$, $P=0.5702$). ANCOVA accounted for 63.2% of the total variance. Virulence is the percentage of non-dormant Bromus tectorum host seeds killed, the mycelia growth index is defined as day-14 colony diameter, and the study is on isolates in two independent growth rate trials (the open vs. closed symbols) at laboratory temperature. The plotted lines are from regression analysis by trial. Analysis of covariance showed that the effect of virulence on MGI (overall regression slope) was highly significant, the slopes of the regression linesfor the two trials were not significantly different and the elevations (y-intercepts) for the two trials were marginally significantly different.

There was a difference in mean MGI between growth rate trials that approached statistical significance ($df=1$, 37, $F=4.04$, $P=0.518$). This mean MGI difference (mean difference in day-14 colony diameter) between trials was 7.85 mm; it is apparent in FIG. 2 as a difference in the elevation of the plotted regression lines. Isolates in the second trial grew more quickly, on average, than those in the first trial. The most likely explanation for this is a difference in mean temperature between the two trials, which took place at laboratory temperature and not in a controlled environment chamber. This interpretation is supported by the fact that two isolates common to both growth rate trials both showed increased growth rates in the second trial. One isolate in the second growth rate trial was anomalous in having a very slow growth rate but also relatively low virulence. This outlier is plotted in FIG. 2 but not included in the analysis. No isolates exhibited both a fast growth rate and high virulence.

Example 3. Slow-Growth Strain is More Effective at Field Loads on Non-Dormant Seeds This example describes a relationship between putative phytotoxin production and virulence between strains of *P. semeniperda*. While only a few *P. semeniperda* strains can cause high mortality on non-dormant cheatgrass seeds, virtually all can cause complete mortality on dormant cheatgrass seeds at artificially high inoculums loads.

Example 2 showed that, when virulence was measured as the ability to kill non-dormant cheatgrass seeds, wide among-strain variation in virulence was evident, with values for non-dormant seed mortality ranging from 4-43%, as shown in FIG. 2. The measurement of mycelial growth rate in culture showed that there was a significant negative correlation between MGI and virulence. The most virulent strains were the slowest-growing, and the least virulent strains were the fastest-growing.

While not intending to be bound by any theory or mechanism of action, our data has suggested that there are at least two types of virulence. A first type (herein referred to as "Type 1") of virulence appears to involve pathogenicity factors involved with initial penetration and host tissue death, and all strains must possess this type at some level to kill a dormant host seed. When an inoculum is applied to dormant seeds at a load that is more similar to a field inoculum load, significant among-strain differences are apparent, with a range of 5-36% seed mortality at 1:6400 inoculum dilution after incubation at 20 C for 2 weeks. This variation represents variation in Type 1 virulence.

A second type (herein referred to as "Type 2") of virulence appears to involve phytotoxins that cripple or disable a non-dormant seed that can potentially germinate and escape. We were excited and surprised to find in our genome assembly the homologues of genes known to regulate biosynthesis of complex phytotoxins called cytochalasins, as cytochalasins are good candidates as causal agents for the Type 2 virulence.

To explore the consequences of the negative relationship between virulence and growth rate further, we inoculated dormant and non-dormant host seeds with both a slow-growing strain with high Type 2 virulence and a fast-growing strain with low Type 2 virulence. We knew from previous work using single sequence repeat (SSR) marker genotyping that co-infections by multiple strains on single seeds are common. By choosing two strains with contrasting SSR fingerprints for the co-infection study, we were able to distinguish the proportion of stromata produced by each strain on co-infected seeds (FIG. 3).

Figure 3:
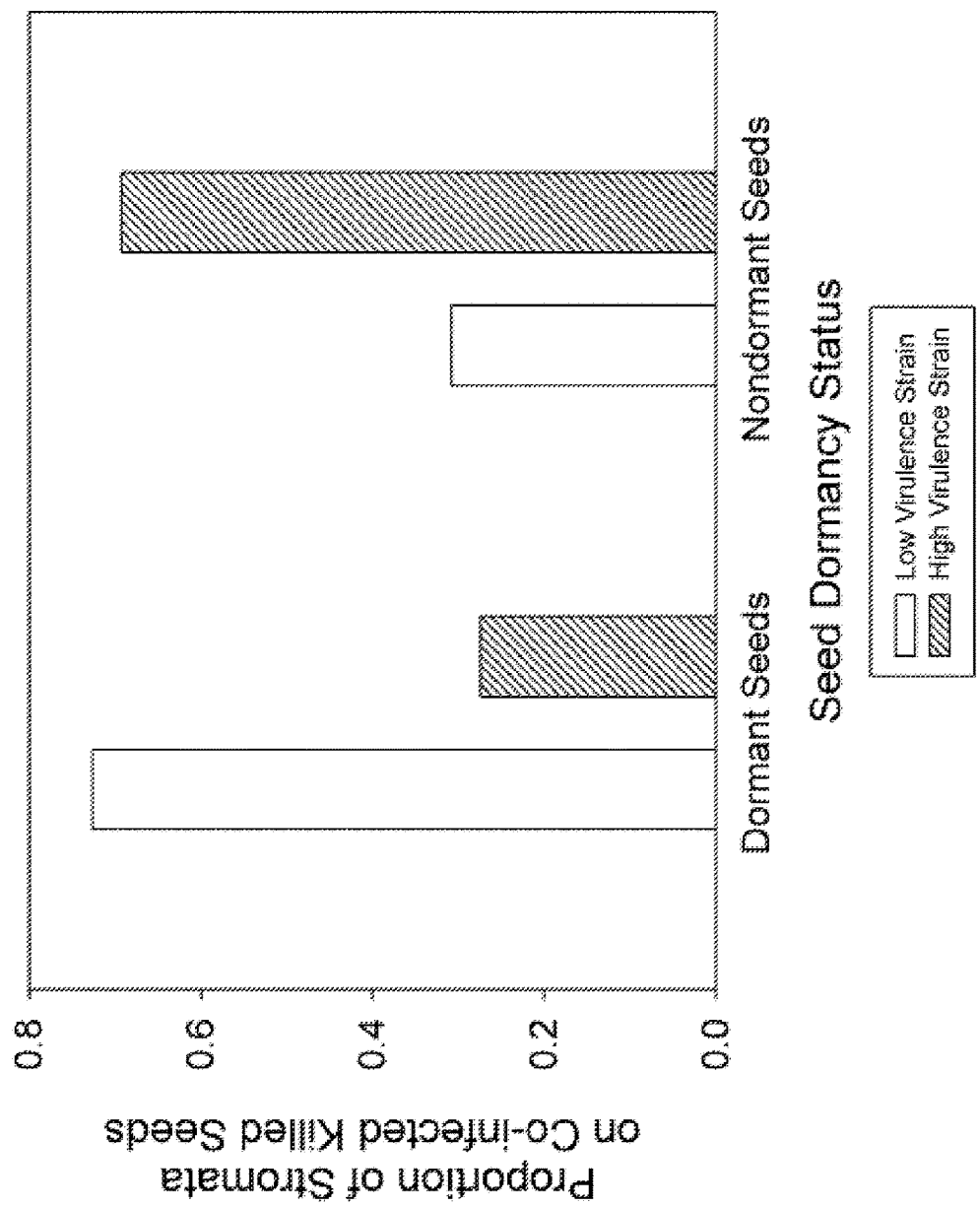
FIG. 3 illustrates the proportion of stromata produced by a 50/50 mix of a strain with high Type 2 virulence and a strain with low Type 2 virulence after co-inoculation onto dormant vs. non-dormant cheatgrass seeds, according to some embodiments.

FIG. 3 illustrates the proportion of stromata produced by a 50/50 mix of a strain with high Type 2 virulence and a strain with low Type 2 virulence after co-inoculation onto dormant vs. non-dormant cheatgrass seeds, according to some embodiments. The data represents the results observed using two strains having contrasting SSR fingerprints in a co-infection study, and distinguishes the proportion of stromata produced by each strain on co-infected seeds.

When we inoculated these two strains onto non-dormant seeds, the strain with high Type 2 virulence and slow growth produced more than twice as many stromata as the fast-growing non-virulent strain. The opposite result was observed on dormant seeds, where the fast-growing non-virulent strain produced more than twice as many stromata as the virulent slow-growing strain. The statistics provide a chi-square of 22.8 and P<0.0001 Without intending to be bound by any theory or mechanism of action, these highly significant results suggest that (i) polymorphism for Type 2 virulence may be maintained in a population by temporally varying selection that results from changes in host seed dormancy status through the season; and (ii) that the two types of virulence are under independent genetic control. It is also appears that (iii) the fast-growing strain may have performed best on dormant seeds because of competitive superiority within the seeds due to its faster growth rate, rather than a superior ability to attack dormant seeds (i.e., higher Type 1 virulence).

Example 4. Production of a Bulk Inoculum

This example describes a way of producing a bulk inoculum. Production of the bulk inoculum can be a five-step process:

1. Because this fungus is a dry-sporulator, conidial inoculum should be produced in solid culture rather than liquid culture, usually a modified alphacell medium agar, though some strains can sporulate better on V8 agar. We have used a previously-published protocol for this conidial production methodology that defines optimum temperature and light conditions (including ultraviolet light; Campbell M A et al., Plant Pathology 52:448-454 (2003)(cited earlier).

However, we have improved upon the methodology by developing a harvest technology that involves washing the conidia from the culture plates onto a sieve with sterile water. The conidia are allowed to dry on the sieve, and are then scraped free, air-dried, and stored in glassine weigh envelopes or vials. This increases conidial yield considerably over the original published method and results in higher-purity spore collections.

2. Conidial inoculum can be tested for germinability, then added to a liquid culture medium (0.1 g of conidia to 7 liters of medium) in a sterilized 10-liter fermenter, which is then subjected to aerated agitation at room temperature (ca. 22 degrees C., an optimum growth temperature for the fungus) for approximately 3 days. The standard liquid medium used is potato dextrose broth. When mycelial balls grown from individual conidia reach approximately 5 mm in diameter, they are aseptically harvested by siphoning into sterile centrifuge bottles, and centrifuged to separate mycelium from spent medium.

3. Centrifuged mycelium produced in submerged fermentation culture can then be mixed with a carrier consisting of a finely granular form of calcined montmorillonite clay (tradename AGSORB) along with supplemental fresh medium to stimulate mycelial growth and spore production during drying. All field trials to date have been carried out using bulk inoculum prepared with potato dextrose broth as the supplemental medium. Mixing is achieved in this small batch system by combining mycelium, supplemental medium, and carrier in a rock tumbler and rotating until the materials are completely mixed.

4. The mixture of mycelium, supplemental medium, and carrier is then spread out in a thin layer (ca. 1-2 cm) in an aluminum pan covered with a clear plastic lid to slow drying, and placed under cool white fluorescent and ultraviolet lights at room temperature for 24-48 hours to stimulate conidial production. It is then moved to another location (usually a greenhouse at 25-30 C) to finish the slowdrying process. The clear plastic lids remain on the drying pans during this process.

5. The bulk inoculum dries into a solid but friable mass with most of the sporulation on the surface exposed to light. The bulk inoculum is then crushed by forcing it through a stiff screen having mesh size of 30/60, such that particles ranging in size from about 0.250 mm to about 0.595 mm are created and thoroughly mixed prior to weighing for application in the field. This bulk inoculum is then evaluated in terms of conidial concentration per weight of inoculum using haemocytometer counts and conidial germinability is tested. The air-dried inoculum has been stored for up to two years unsealed under laboratory conditions with no apparent loss or viability.

Example 5. Durability and Stability of the Bulk Inoculum

It is highly desirable to have an inoculum that is durable during storage and use. This example shows that the inoculum formulations taught herein are very durable and stable.

We currently have two years of data on bulk inoculum stored dry (32% humidity in sealed containers) at three temperatures: freezing (−20 C), refrigerated (−4 C), and room (20 C). We tested the infectivity of the inoculum every three months by sprinkling known small quantities on replicated sets of 50 dormant cheatgrass seeds on wet blotters in petri dishes, then incubating at 20 C for four weeks and scoring the proportion of killed seeds. To date there has been no loss of infectivity of the inoculum under any of the storage conditions; seed mortality not significantly different from 100% has been observed in every case. We conclude that dry formulations of this biocontrol agent will have a long shelf life under a range of conditions.

Moreover, the inoculum formulations are stable in the field. They have worked in conditions as wet as where winter wheat is grown, to conditions as dry as the Mojave Desert. They even survive fire. We initiated a series of studies to learn how both cheatgrass seeds in the seed bank and the fungal pathogen *P. semeniperda* respond to fire. Results from a thermal death point experiment showed that pathogen propagules were killed at a higher temperature than cheatgrass seeds, indicating that it would be better able to survive fire. Pyrometer measurements from controlled field burns indicated that temperatures high enough to kill seeds or pathogen propagules via radiant heat were rarely reached, especially if seeds or propagules were at the base of the litter or below the soil surface. Ring bioassays and seed bank sampling before and after fire supported these conclusions.

This example provides results that teach away from the current state-of-the-art expectations for a mycoherbicide. One of skill would not expect a mycoherbicide to have this long of a shelf-life, such a long window of application, or such resilience to the elements.

Example 6. Field Trials on Western and Central Utah Cheatgrass Sites

This example illustrates the effect of an administration of *Pyrenophora semeniperda* on Utah cheatgrass sites. Seed banks from two Utah sites, one in western Utah (Davis Mountain) and one in central Utah (Santaquin Canyon), were investigated.

The ability of the inoculum to decrease the proportion of viable seeds in the persistent (carryover) seed bank was measured at the end of spring, following an administration in the fall. A range of inoculum loads was studied.

Figure 4:
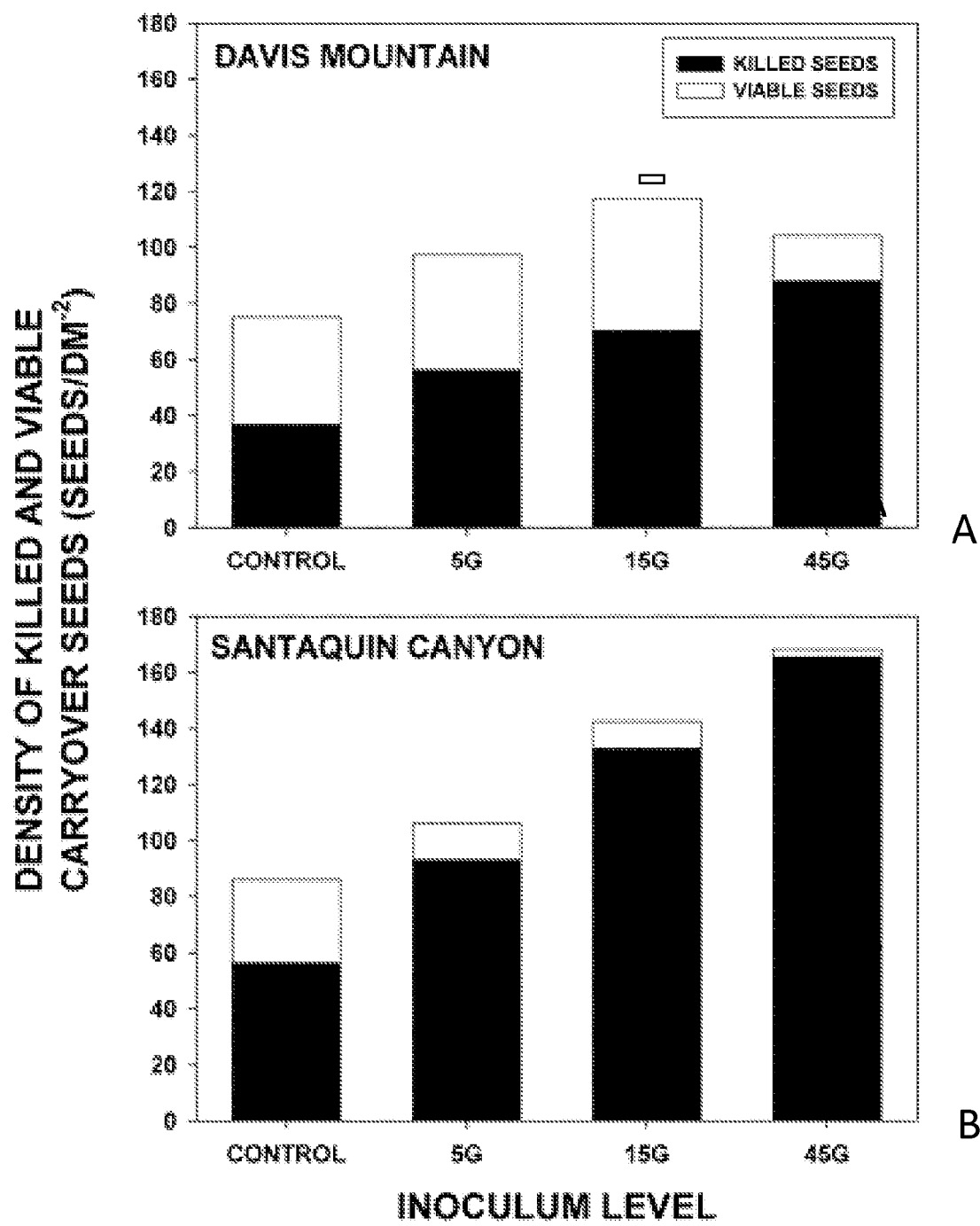
FIGS. 4A and 4B illustrate the density of killed and viable carryover cheatgrass seeds in Utah seed banks as a function of the administered dose of a *P. semeniperda* inoculum, according to some embodiments.
Figure 5:
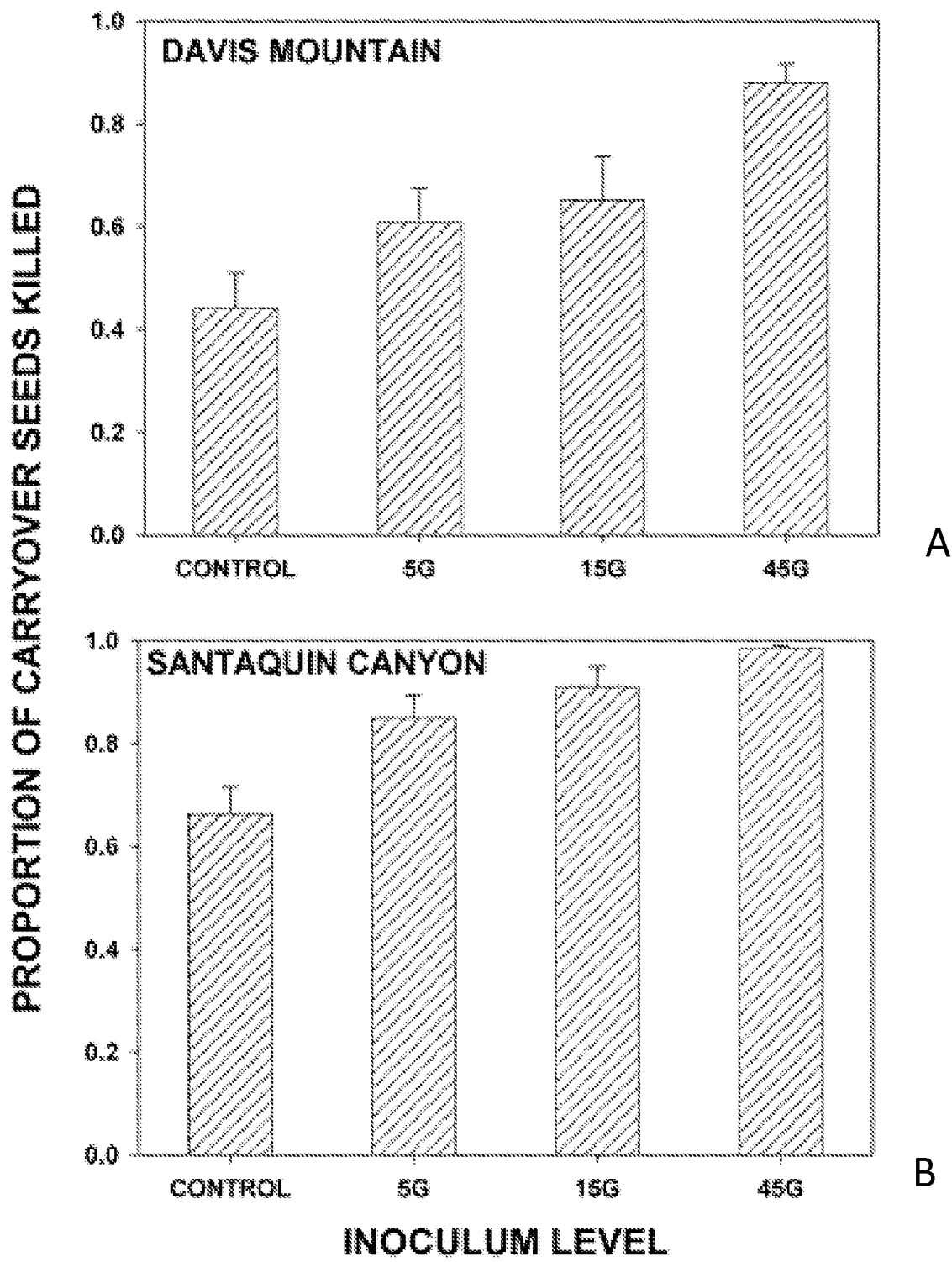
FIGS. 5A and 5B illustrate the proportion of carryover cheatgrass seeds in Utah seed banks killed as a function of the administered dose of a *P. semeniperda* inoculum, according to some embodiments.

FIGS. 4A and 4B illustrate the density of killed and viable carryover seeds in Utah seed banks as a function of the administered dose of a *P. semeniperda* inoculum, according to some embodiments. FIGS. 5A and 5B illustrate the proportion of carryover cheatgrass seeds in Utah seed banks killed as a function of the administered dose of a *P. semeniperda* inoculum, according to some embodiments. It can be seen that, in both locations, the inoculums decreased the proportion of viable seeds in the persistent (carryover) seed bank at the end of spring following a fall application of the inoculums. In most cases, the density of killed seeds was greatly increased, particularly at higher inoculums loads.

It can be seen that the application of high loads (45 g) of the inoculums virtually doubled the density of killed seeds in the seed bank. Densities are presented as seeds per $dm^2$; densities per $m^2$ would be 100 times these values. We achieved 93% and 98% control of the seed banks in these locations.

The strain used in these experiments was WRK0, a strain obtained from a seed bank sample in Skull Valley, Utah, about 10 miles north of the Davis Mountain site. Bulk inoculum was produced as described earlier and applied at rates of 5 g, 15 g, and 45 g to square foot plots in September into dense monoculture stands of cheatgrass. This bulk inoculum was not evaluated quantitatively, but visual inspection indicated high levels of conidial production. The experiment was a randomized block design with ten replications. Uninoculated control plots were included for comparative purposes. A seed bank sample was obtained from each plot in the spring after all germination was complete but prior to the dispersal of current year seeds as described earlier, and densities of viable and pathogen-killed seeds were determined. The level of control obtained is defined as the proportion of the potential carryover seed bank (viable plus killed seeds) that was killed by the pathogen. As the pathogen is naturally occurring on these sites, even the uninoculated plots exhibit some level of control. The success of the inoculum treatment is indicated by both the absolute kill proportion and the increase in kill proportion over the uninoculated plots.

Example 7. Field Trial on a Southern Utah Red Brome Site

This example illustrates the effect of an administration of *Pyrenophora semeniperda* on a red brome site in southern Utah. A seed bank at Lytle Ranch Field Experimental Station was investigated.

Figure 6:
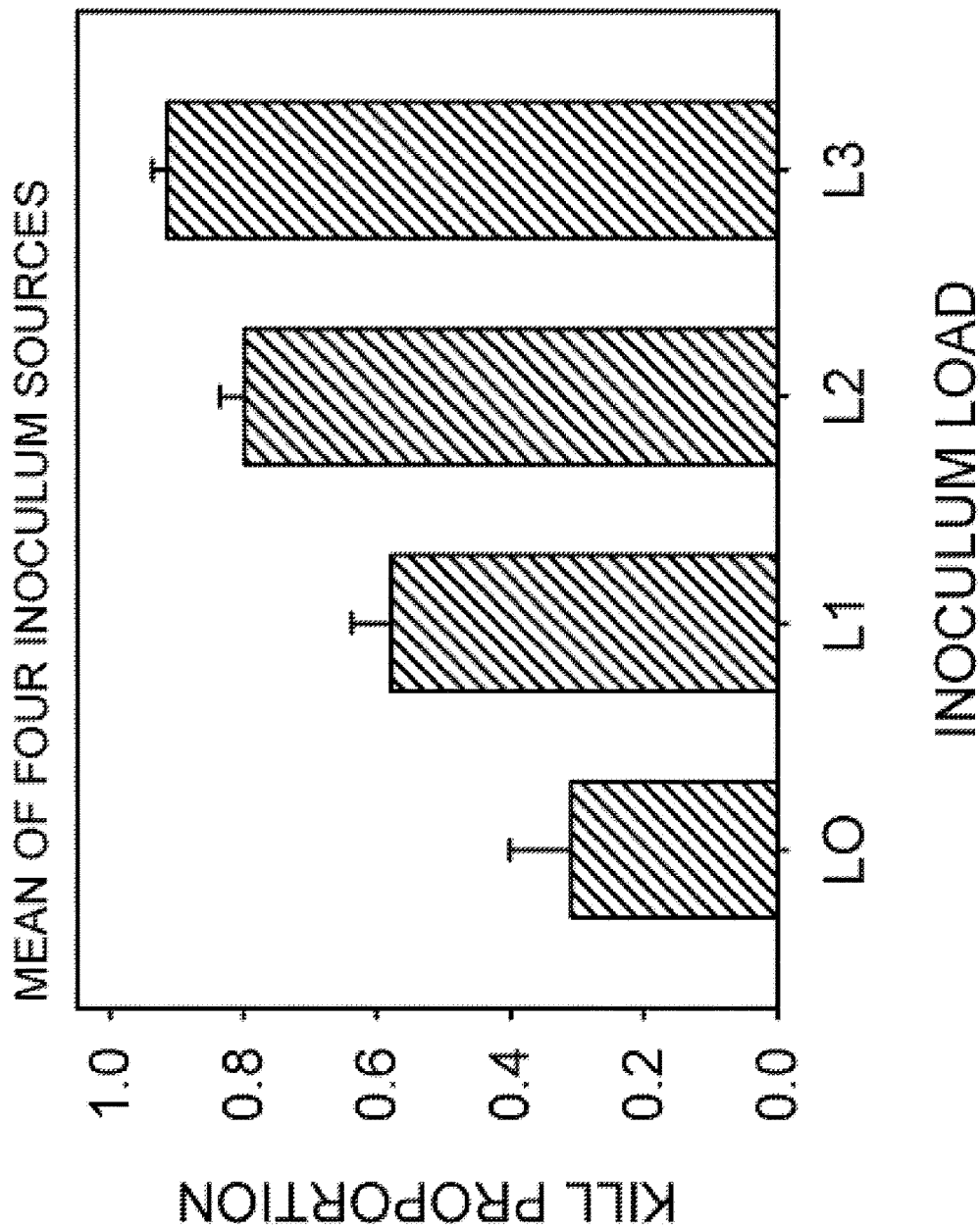
FIG. 6 illustrates proportion of carryover red brome seeds killed as a function of the administered dose of a *P. semeniperda* inoculum, according to some embodiments.

FIG. 6 illustrates proportion of carryover red brome seeds killed as a function of the administered dose of a *P. semeniperda* inoculum, according to some embodiments. In this example, it can be seen that the application of high loads of the inoculum virtually tripled the kill proportion in the seed bank. We achieved a 95% control of the seed bank in at this location. The figure represents the mean effect of four strains: WRK0 as used in the earlier test, two strains from Tenmile Creek, Utah (TMC16 and TMC23), and a strain from Dog Valley, Utah (DOG3). Conidial concentration was not quantified, but conidial production was determined by inspection to be high in all four bulk inocula. The design was a randomized block design with ten replications similar to the experiment previous year. There were small significant differences in efficacy among strains, but all showed similar trends. L0 through L3 labels on the x-axis correspond to control, 5 g, 15 g, and 45 g inoculum applications.

Example 8. Field Trial on a Central Washington Cheatgrass Site that Includes Co-Administration of Burning This example illustrates the effect of an administration of *Pyrenophora semeniperda* on a cheatgrass site in central Washington, as well as the effect of a co-administration of burning prior to administering the inoculum. A seed bank at Haven Flats was investigated. The protocols followed were similar to those described for the Lytle Ranch red brome study, and the same inoculum sources were used. The main difference was the addition of a burn treatment. The design was a split-plot design with burn as the main plot and inoculum sources and levels randomized within subplots. The burn was a controlled burn in late spring; its main point was to find out if the microenvironment created by burning was more or less favorable to the pathogen than the microenvironment in unburned cheatgrass.

Figure 7:
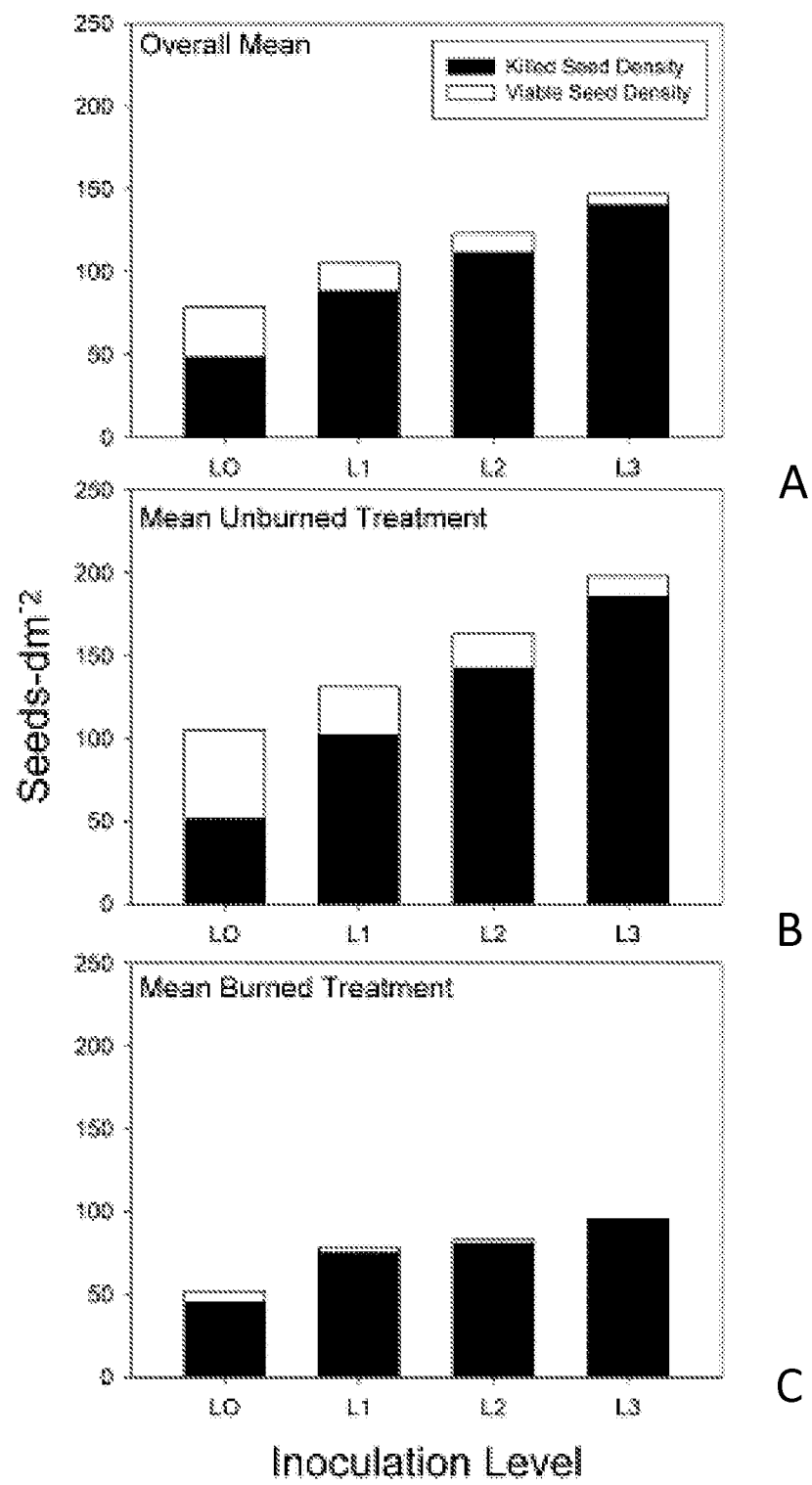
FIGS. 7A-7C illustrate the density of killed and viable carryover cheatgrass seeds in burned and unburned treatments for a Washington seed bank as a function of the administered dose of a *P. semeniperda* inoculum, according to some embodiments.

FIGS. 7A-7C illustrate the density of killed and viable carryover cheatgrass seeds in burned and unburned treatments for a Washington seed bank as a function of the administered dose of a *P. semeniperda* inoculum, according to some embodiments. Axis labels are as described above for the Lytle Ranch study, and graphed values again represent the means of four strains.

Burning decreased the total size of the potential carryover seed bank, making the goal of complete control more achievable, and also slightly increased the efficacy of the biocontrol treatments (significant burn×inoculum level interaction for killed seed proportion; $p=0.0006$). As can be seen from FIG. 7, we achieved complete elimination (100%) of the persistent seed bank in treatments that included burning prior to inoculum application, a common scenario for post-fire rangeland restoration. In unburned treatments, we achieved >90% control.

Example 9. Field Trials on Brome Grass that Includes Co-Administration of Herbicides Herbicide treatments in trials with Roundup (glyphosate) or Plateau (imazapic) gave essentially complete control of the emerging/emerged annual brome stand, but had no measurable effect on the efficacy of pathogen inoculum, indicating that these types of treatments could be successfully combined for annual brome control. These experiments were carried out at three sites in (Pakoon, a red brome site in northern Arizona, Whiterocks, a cheatgrass site in Skull Valley, Utah, and Haven Flats, a cheatgrass site in central Washington. They utilized protocols similar to those described above, and a split plot design with herbicide treatment as the main plot and inoculum source and level as the subplots. Two inoculum sources were used: WRK01 and DOG3, and these were applied at two levels (5 g and 15 g). Significant increases in the proportion of killed seeds were observed with inoculum application at all three sites, and there was no significant interaction with herbicide treatment at any site.

Ring bioassays to evaluate the impact of residual inoculum a year after application showed a measurable but small negative effect on emergence of one of two perennial grass species (bluebunch wheatgrass; reductions <15%). The ring bioassays followed the protocol of Beckstead et al., Journal of Ecology (1) 98:168-177 (2010), cited earlier. The other species, bottlebrush squirreltail, was not significantly affected. These ring bioassays were carried out with ring samples from the studies, with similar results. These results demonstrate that inoculum loads that are effective at reducing annual brome seed banks pose little or no risk to native grass species.

Example 10. Inhibiting a Brome Grass Stand Through an Infection of Surviving Brome Seeds that Develop into the Stand One surprising result of our first round of field inoculations was a sometimes significant reduction in standing biomass at high inoculum loads, which suggested that the pathogen can grow endophytically in plants from surviving infected seeds and negatively impact their growth. We successfully isolated the organism from cheatgrass leaf tissue after inoculating non-dormant seeds, showing that that the organism can be an endophyte, and we obtained reductions in seedling growth from inoculated seeds for cheatgrass as well as native grass species. *Festuca idahaensis* and *Bouteloua curtipendula* showed no difference in seedling biomass between infected and non-infected seedlings, whereas *Bromus tectorum* suffered a 10% reduction in growth and *Agropyron dasystachyum* growth was reduced 35%. This suggests that, surprisingly, the pathogen can negatively impact native species beyond simple seed mortality. It is worthy to note that one of skill should find that this was a highly unexpected result.

Example 11. Using a Mix of Strains of *P. Semeniperda* in a Biocontrol Formulation Our data in FIG. 3 suggests that different strains of the biocontrol pathogen have different types of virulence that target different subsets of the host brome seed population. This example discusses how different strains could potentially have contrasting and possibly complementary effects in field inoculations.

1) Using a fast-growing strain with high Type 1 virulence (ability to cause mortality of dormant seeds at low inoculum loads), but low Type 2 virulence (ability to cripple germinating seeds) would effectively target dormant brome seeds in the carryover seed bank but would be unlikely to kill significant numbers of non-dormant host seeds. A fast-growing strain with low Type 2 virulence would also be predicted to have minimal effect on non-target host seeds, a desirable trait.

2) Using a slow-growing strain with high Type 2 virulence would target rapidly germinating, non-dormant seeds but could be less effective on dormant seeds at low inoculum loads, depending on its Type 1 virulence. Such a slow-growing strain with high Type 2 virulence would pose the biggest threat to non-target host seeds, many of which germinate relatively slowly even when non-dormant.

3) By using a mixture of a slow-growing strain with high Type 2 virulence but low Type 1 virulence and a fast-growing strain with high Type 1 virulence but low Type 2 virulence, we would effectively target both non-dormant and dormant brome seeds. In addition, because the fast strain would have a competitive advantage on dormant seeds and therefore be likely to produce a large fraction of the resulting conidial propagules, the subsequent risk to non-target host seeds would be substantially reduced.

4) To prepare a multiple-strain mixture, the individual strains would be produced on carriers in separate batches, then mixed together as dry bulk inoculum. This would prevent competitive effects during culturing from favoring the fast-growing strains and biasing the composition of the mixture. In this way, mixtures of any proportion or combination of strains could be prepared.

Example 12. Field Testing Formulations of the Biocontrol Agent *Pyrenophora Semeniperda* on Red Brome (*Bromus rubens*) at the Pakoon Study Site in Northwestern Arizona This example provides results from a field test of formulations of the biocontrol agent *Pyrenophora semeniperda* on red brome (*Bromus rubens*) at the Pakoon Study Site in northwestern Arizona. The formulations were tested at an inoculum load of 10 gram-equivalents per square foot, which is known to be insufficient for complete control, in order to maximize the probability of detecting formulation treatment differences. This field test included two strains used in earlier trials (TMC23 and DOG3) as well as four new strains (TMC1022, WRK1022, WRR1016, and WRR1029) and a mixture of one fast-growing strain (WRR1029, 65.8 mm colony diameter at 14 days under earlier-described test conditions) and one slow-growing strain (WRR1016, 39.8 mm diameter at 14 days). There were no significant differences in seed mortality among strains in this test.

Values are averaged across burned and unburned treatments. All inoculation treatments increased the killed seed proportion significantly over the uninoculated control (30% mortality).

Formulations:

Formulations were prepared according to the protocol described herein, with the following modifications.

a. Original formulation—calcined montmorillonite clay carrier with potato dextrose broth as the supplemental nutrient medium added before drying;
  b. Original carrier with MAM supplement—original formulation with calcined montmorillonite clay carrier, but using the MAM broth (modified alphacel medium comprised of coconut milk and oatmeal) supplement instead of the PDB supplement, because the MAM supplement induced more sporulation in culture than the PDB supplement; and,
  c. Lightweight carrier with MAM supplement—original formulation, but (i) using the MAM supplement instead of the PDB supplement, and also (ii) using fine grade vermiculite as a lighter carrier instead of the heavier calcined montmorillonite;

Results:

a. Original formulation—application of the original formulation resulted in 67% mortality;

b. Original carrier with MAM supplement—surprisingly, application of the MAM supplement instead of the PDB supplement resulted in a significantly increased mortality of 83%; and, c. Lightweight carrier with MAM supplement—very surprisingly, combining the MAM supplement with a lightweight vermiculite carrier resulted in mortality equivalent to that achieved with MAM supplement on the heavier original carrier.

The vermiculite had a size of up to 3 mm maximum dimension before processing. After processing, most of the particles fell into the <1 mm range in size. After application of the liquid inoculum to the particles, and after drying, grinding, and sieving of the inoculum covered particles, the maximum size was <2 mm.

Figure 8:
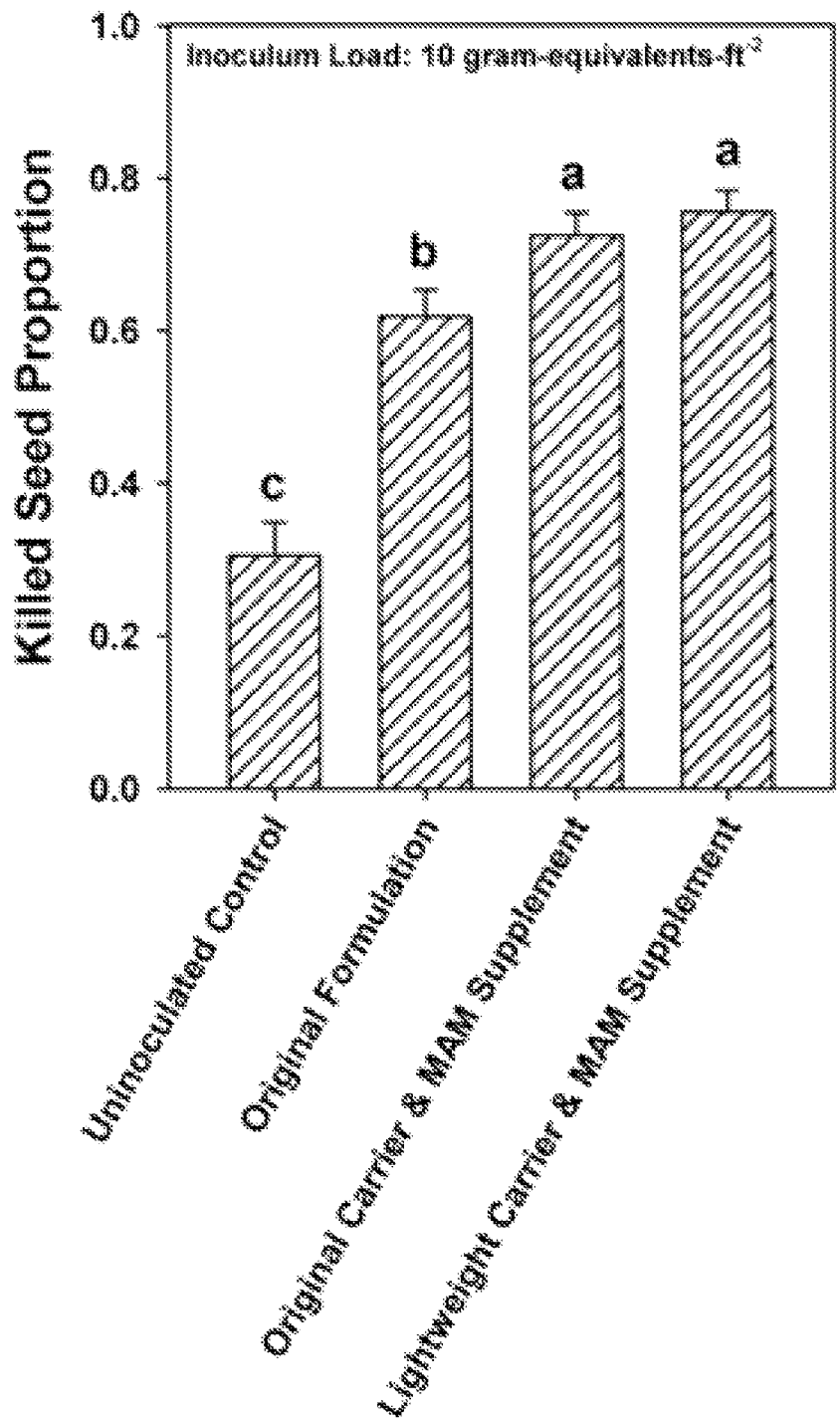
FIG. 8 shows the results of the formulation field test comparisons, according to some embodiments.

FIG. 8 shows the results of the formulation field test comparisons, according to some embodiments. It was surprising to see that the MAM supplement induced more sporulation in culture than the PDB supplement; and, as a result, quite pleasing to see the significantly increased mortality obtained by simply using the MAM supplement instead of the PDB supplement. Using the lighter vermiculite in combination with the MAM supplement, however, gave a very surprising result. Since vermiculite has a bulk density that is one quarter of the bulk density of the original clay carrier, it was very pleasing to see that the lightweight vermiculite carrier was just as effective as the heavier, original carrier in delivering the inoculum to the seeds. Accordingly, one of skill in the art will certainly appreciate the innovations and observations taught herein, for at least the reason that these two formulation improvements have resulted in a highly beneficial five-fold reduction in the weight of inoculum needed to achieve a given level of control.

It should be appreciated that the experimental conditions and components provided herein are for illustration and example only. One of skill can vary the experimental conditions and components to suit a particular or alternate experimental design. The experimental conditions can be in the lab or in the field, or designed for any target, for example, any invasive species, brome or otherwise. For example, botanical testing can be varied to suit a desired experimental method.

We claim:

1. An agricultural, mycoherbicide formulation for killing ungerminated seeds of invasive grass species, comprising a mixture of:

an effective amount of a slow-growing strain of *Pyrenophora semeniperda*, characterized in that it is limited to reaching a mycelial colony diameter of <50 mm after 14 days at about 20° C. on quarter-strength potato dextrose agar from a single conidial inoculation, mixed with modified alphacel medium (MAM);

an effective amount of a fast-growing strain of *Pyrenophora semeniperda*, characterized in that it reaches a mycelial colony diameter of >65 mm after 14 days at about 20° C. on quarter-strength potato dextrose agar from a single conidial inoculation, mixed with MAM.

2. The formulation of claim 1, wherein the invasive grass species comprises *Bromus arvensis, Bromus diandrus, Bromus tectorum, Bromus rubens*, or *Taeniatherum caput-medusae*.

3. The formulation of claim 1, wherein the invasive grass species comprises *Bromus arvensis, Bromus diandrus*, or *Taeniatherum caput-medusae*.

4. The formulation of claim 1, wherein the invasive grass species comprises *Bromus tectorum*.

5. The formulation of claim 1, wherein the invasive grass species comprises *Bromus rubens*.

6. The formulation of claim 1, wherein the formulation further comprises calcined montmorillonite clay or vermiculite.

7. The formulation of claim 1, wherein the formulation is formulated as granules; a wettable powder; an emulsifiable concentrate, powder, or dust; a flowable; a solution; a suspension; an emulsion; or a controlled release formulation.

8. A method of treating soil to kill ungerminated seeds of invasive grass species, the method comprising administering an effective amount of the mycoherbicide formulation of claim 1 to soil in need of treatment.

9. The method of claim 8, wherein the invasive grass species comprises *Bromus arvensis, Bromus diandrus, Bromus tectorum, Bromus rubens*, or *Taeniatherum caput-medusae*.

10. The method of claim 8, wherein the method further comprises co-administering a burn, a tillage, a pre-emergent herbicide, and a post emergent herbicide, an additional mycoherbicide, or a bacterial biocontrol.

11. The method of claim 10, wherein the co-administration is done before or after the administration of the formulation.

12. The method of claim 10, wherein the co-administration is done during the administration of the formulation.

* * * * *